(12) United States Patent
Engh et al.

(10) Patent No.: US 9,403,896 B2
(45) Date of Patent: Aug. 2, 2016

(54) SERPIN-FINGER FUSION POLYPEPTIDE

(71) Applicant: Hoffmann-La Roche Inc., Nutley, NJ (US)

(72) Inventors: Richard Engh, Tromsoe (NO); Erhard Kopetzki, Penzberg (DE); Tilman Schlothauer, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 13/830,255

(22) Filed: Mar. 14, 2013

(65) Prior Publication Data

US 2014/0045742 A1 Feb. 13, 2014

Related U.S. Application Data

(63) Continuation of application No. PCT/EP2011/065884, filed on Sep. 13, 2011.

(30) Foreign Application Priority Data

Sep. 14, 2010 (EP) .................................... 10176617

(51) Int. Cl.
*C07K 14/00* (2006.01)
*C07K 14/81* (2006.01)
*C07K 14/005* (2006.01)

(52) U.S. Cl.
CPC ............... *C07K 14/81* (2013.01); *C07K 14/001* (2013.01); *C07K 14/005* (2013.01); *C07K 14/8121* (2013.01); *C07K 14/8125* (2013.01); *C07K 14/8128* (2013.01); *C07K 2319/01* (2013.01); *C07K 2319/70* (2013.01); *C12N 2740/16122* (2013.01)

(58) Field of Classification Search
CPC .. C07K 14/001; C07K 14/81; C07K 14/8121; C07K 14/8125; C07K 14/8128; C07K 2319/01; C07K 2319/70; C07K 14/005; C07K 14/162
See application file for complete search history.

(56) References Cited

U.S. PATENT DOCUMENTS

| | | | |
|---|---|---|---|
| 5,464,933 A | 11/1995 | Bolognesi et al. | |
| 5,656,480 A | 8/1997 | Wild et al. | |
| 6,013,263 A | 1/2000 | Barney et al. | |
| 6,017,536 A | 1/2000 | Barney et al. | |
| 6,060,065 A | 5/2000 | Barney et al. | |
| 6,093,794 A | 7/2000 | Barney et al. | |
| 6,258,782 B1 | 7/2001 | Barney et al. | |
| 6,348,568 B1 | 2/2002 | Barney et al. | |
| 6,479,055 B1 | 11/2002 | Bolognesi et al. | |
| 6,656,906 B1 | 12/2003 | Barney et al. | |
| 6,849,605 B1 | 2/2005 | Shapiro | |
| 2006/0040867 A1 | 2/2006 | Shapiro | |
| 2010/0210528 A1* | 8/2010 | Shapiro | 514/12 |

FOREIGN PATENT DOCUMENTS

| | | |
|---|---|---|
| EP | 0355905 A1 | 2/1990 |
| EP | 0147761 B1 | 8/1990 |
| EP | 0927764 A2 | 11/1998 |
| EP | 0972838 B1 | 9/2004 |
| JP | 2004-537970 | 12/2004 |
| JP | 2007-503838 | 3/2007 |
| WO | 96/19495 | 6/1996 |
| WO | 96/40191 | 12/1996 |
| WO | 97/24453 | 7/1997 |
| WO | 99/59615 | 11/1999 |
| WO | 00/52034 | 9/2000 |
| WO | 00/69902 | 11/2000 |
| WO | 01/03723 A1 | 1/2001 |
| WO | 01/51673 A1 | 7/2001 |
| WO | 02/058638 A2 | 8/2002 |
| WO | 02/063017 A2 | 8/2002 |
| WO | WO 03066078 A1 * | 8/2003 ........... C07K 14/765 |
| WO | 2005/067960 A1 | 7/2005 |
| WO | WO 2008110332 A1 * | 9/2008 |
| WO | 2009/012944 A1 | 1/2009 |

OTHER PUBLICATIONS

Jan Munch, Discovery and Optimization of a Natural HIV-1 Entry Inhibitor Targeting the gp41 Fusion Peptide, Cell 129, 263-275, Apr. 20, 2007, pp. 263-275.*
ABBKS Linker, Protein Domains/Linkers, parts.igem.org/Protein_domains/Linker, 2009.*
Benedicte Py, The Phospholipid Scramblases 1 and 4 Are Cellular Receptors for the Secretory Leukocyte Protease Inhibitor and Interact with CD4 at the Plasma Membrane, PLOS One, Mar. 2009, vol. 4, Issue 3, pp. 1-11.*
Ricardo Moro-Vidal, Alpha-Fetoprotein Receptor:A Widespread Cancer Marker of Clinical PotentialCurex Technologies Inc., 2003.*
Baumann et al., "Crystal Structure of Cleaved Equine Leucocyte Elastase Inhibitor Determined at 1•95 Å Resolution" J. Mol. Biol. 226:1207-1218 ( 1992).
Baumann et al., "Crystal Structure of Cleaved Human $\alpha_1$-Antichymotrypsin at 2.7 Å Resolution and Its Comparison with Other Serpins" J. Mol. Biol. 218:595-606 ( 1991).

(Continued)

Primary Examiner — James H Alstrum Acevedo
Assistant Examiner — Erinne Dabkowski
(74) Attorney, Agent, or Firm — James E. Nesbitt

(57) ABSTRACT

The current invention comprises a fusion polypeptide comprising a serpin-finger polypeptide conjugated to a biologically active polypeptide optionally via a peptidic linker polypeptide. Another aspect is a protein complex of the serpin-finger fusion polypeptide and a serpin, wherein the fusion polypeptide is incorporated in the serpin into the middle of beta-sheet A as strand 4a. Also an aspect of the current invention is the in vitro preparation of the protein complex. The serpin-finger polypeptide targets and anchors the biologically active polypeptide with high affinity and functional spatial orientation.

22 Claims, 5 Drawing Sheets

(56) References Cited

OTHER PUBLICATIONS

Congote, "Multi-Functional Anti-HIV Agents Based on Amino Acid Sequences Present in Serpin C-Terminal Peptides" Anti-Infective Agents in Medicinal Chemistry 7:126-133 (2008).

Loebermann et al., "Human $\alpha_1$-Proteinase Inhibitor: Crystal Structure Analysis of Two Crystal Modifications, Molecular Model and Preliminary Analysis of the Implications for Function" J. Mol. Biol. 177:531-557 (1984).

Mourey et al., "Antithrombin III: structural and functional aspects" Biochimie 72:599-608 (1990).

Mourey et al., "Crystal Structure of Cleaved Bovine Antithrombin III at 3•2 Å Resolution" Journal of Molecular Biology 232(1):223-241 (Jul. 1993).

Qi et al., "Rationally Designed Anti-HIV Peptides Containing Multifunctional Domains as Molecule Probes for Studying the Mechanisms of Action of the First and Second Generation HIV Fusion Inhibitors" The Journal of Biological Chemistry 283(44):30376-30384 (Oct. 2008).

Schechter et al., "On the Size of the Active Site in Proteases. I. Papain" Biochem Bioph Res Co 27(2):157-162 (Apr. 1967).

Schulze et al., "Structural transition of $\alpha_1$-antitrypsin by a peptide sequentially similar to β-strand s4A" Eur. J. Biochem. 194:51-56 (1990).

Extended European search report for EP 10000620.4-2401 (Feb. 26, 2010).

Schulze et al., "Structural aspects of serpin inhibition" FEBS Letters 344:117-124 (1994).

Congote, "The C-terminal 26-residue peptide of serpin A1 is an inhibitor of HIV-1" Biochemical and Biophysical Research Communications 343:617-622 (2006).

Schulze et al., "Evidence for the Extent of Insertion of the Active Site Loop of Intact $\alpha_1$ Proteinase Inhibitor in β-Sheet A" Biochemistry 31:7560-7565 (1992).

Ji et al., "CD4-anchoring HIV-1 Fusion Inhibitor with Enhances Potency and in Vivo Stability" J. Biol. Chem. 284:5175-5185 (2009).

Extended European search report for EP 10163454.1-2405 (Jul. 2, 2010).

International Search Report and Written Opinion for PCT/EP2011/065884 (Dec. 9, 2011).

Skinner et al., "Implications for Function and Therapy of a 2.9 Å Structure of Binary-complexed Antithrombin" J. Mol. Biol. 283:9-14 (1998).

US 6,020,459, 02/2000, Barney et al. (withdrawn)

* cited by examiner

SERPIN-FINGER FUSION POLYPEPTIDE

CROSS REFERENCE TO RELATED APPLICATIONS

This application is a continuation of International Application No. PCT/EP2011/065884, having an international filing date of 13 Sep. 2011, the entire contents of which are incorporated herein by reference, and which claims benefit under 35 U.S.C. 119 to European Patent Application No. 10176617.8 filed 14 Sep. 2010.

The current invention is directed to fusion polypeptides comprising a serpin-finger polypeptide and a second peptide, polypeptide or protein as well as the use of such fusion polypeptides.

SEQUENCE LISTING

The instant application contains a Sequence Listing submitted via EFS-Web and hereby incorporated by reference in its entirety. Said ASCII copy, created on Jan. 15, 2015, is named P4720C1_SL.txt, and is 33,737 bytes in size.

BACKGROUND OF THE INVENTION

Serine protease inhibitors (serpins) regulate a multitude of physiological pathways, e.g. inflammation, coagulation, fibrinolysis, apoptosis and extracellular matrix remodeling. The reactive loop of a serpin is cleaved by the serine protease and the serine protease is inactivated via disruption of the catalytic site.

Alpha1-antitrypsin is a 394 amino acid, 52 kDa, glycoprotein synthesized by hepatocytes, macrophages and intestinal and bronchial epithelial cells. Crystal structures show that alpha1-antitrypsin is consisting of five beta-sheets, nine alpha-helices and an exposed mobile reactive loop comprising 14 residues that presents a peptide sequence as a pseudo-substrate for the target protease. Cleavage of the scissile reactive bond, denoted as P1-P1' results in an irreversible conformational change wherein the N-terminal residue of the loop being completely incorporated into the middle of the beta-sheets of alpha1-antitrypsin as strand 4a (Schechter, I., and Berger, A., Biochem. Biophys. Res. Commun. 27 (1967) 157-162; Loebermann, H., et al., J. Mol. Biol. 177 (1984) 531-557; Baumann, U., et al., J. Mol. Biol. 218 (1991) 595-606; Baumann, U., et al., J. Mol. Biol. 226 (1992) 1207-1218; Mourey, L., et al., Biochim. 72 (1990) 599-608; Mourey, L., et al., J. Mol. Biol. 232 (1993) 223-241).

After proteolytic cleavage by its target protease, P1 Met and P1' Ser are separated and the unprimed active site loop is inserted as strand 4a in the antiparallel beta-sheet A. A peptide with the amino acid sequence of strand 4a, residues 345-358 of human alpha1-antitrypsin Thr-Glu-Ala-Ala-Gly-Ala-Met-Phe-Leu-Glu-Ala-Ile-Val-Met, (Seq ID NO: 89), associates with intact alpha1-antitrypsin and forms a stoichiometric complex with properties similar to cleaved alpha1-antitrypsin (Schulze, A. J., et al., Eur. J. Biochem. 194 (1990) 51-56).

In WO 97/024453 receptor specific chimeric viral surface polypeptides for viral and particle incorporation and internalization in target cells are reported. A covalently attached complex of alpha1-antitrypsin-protease inhibitor with a water soluble polymer is reported in EP 0 147 761. In US 2006/0040867 inhibitors of serine protease activity and their use in methods and compositions for treatment of bacterial infections are reported.

Schule, A. J., et al., report structural transition of alpha1-antitrypsin by a peptide sequentially similar to beta-strand S4A (Eur. J. Biochem. 194 (1990) 51-56). Multifunctional anti-HIV agents based on amino acid sequences present in serpin C-terminal peptides are reported by Congote, L. F., in Anti-infective agents in medicinal chemistry, Bentham Science publishers, Hilversum (NL), 7 (2008) 126-133. Qi, Z., et al. (J. Biol. Chem. 283 (2008) 30376-30384) report rationally-designed anti-HIV peptides containing multifunctional domains as molecule probes for studying the mechanism of action of the first and second generation HIV fusion inhibitors. Methods and compositions for inhibition of membrane fusion-associated events, including HIV transmission, are reported in WO 01/51673. In WO 02/063017 integrin-binding chimeras are reported. Heparin fragments and fractions with anti-HIV action are reported in EP 0 355 905. In WO 00/52034 and U.S. Pat. No. 6,849,605 inhibitors of serine protease activity, methods and compositions for treatment of viral infections are reported.

SUMMARY OF THE INVENTION

It has been found that a serpin-finger polypeptide has to have a minimal number of amino acid residues in order to allow for a sufficiently fast association with a serpin. Additionally it has been found that it is beneficial that the amino acid residue at amino acid position 2 of the serpin-finger polypeptide (counted from the N-terminus of the serpin-finger polypeptide) is glutamic acid.

Herein is reported a serpin-finger fusion polypeptide comprising
a serpin-finger polypeptide, and
a further polypeptide,
wherein the further polypeptide can be any polypeptide exerting a biological activity, such as inhibition, activation, binding or labeling.

In one embodiment the serpin-finger fusion polypeptide comprises in addition at least one of
a peptidic linker polypeptide,
a protease cleavage site,
a tag.

In one embodiment the amino acid sequence of the serpin-finger polypeptide is selected from AGAMFLEAIVM (SEQ ID NO: 01), AAGAMFLEAIVM (SEQ ID NO: 02), TEAA-GAMFLEAIVM (SEQ ID NO: 03), AGAMFLEAIVM (SEQ ID NO: 04), TEAAGAMFFEAIPM (SEQ ID NO: 05), TAV-VIA (SEQ ID NO: 06), SEAAASTAVVIA (SEQ ID NO: 07), TEAAGATAVVIA (SEQ ID NO: 08), TDAAGATAVVIA (SEQ ID NO: 09), SDAAGAMFLEAI (SEQ ID NO: 10), or SEAAASMFLEAI (SEQ ID NO: 11). In one embodiment the amino acid sequence of the serpin-finger polypeptide is selected from SEAAASTAVVIA (SEQ ID NO: 07) and SEAAASMFLEAI (SEQ ID NO: 11).

In one embodiment the amino acid sequence of the peptidic linker polypeptide is GGSGG (SEQ ID NO: 12), or SGGGGSGGGGSGGGGT (SEQ ID NO: 52), or STT (SEQ ID NO: 75).

In one embodiment the amino acid residue at amino acid position 2 of the serpin-finger polypeptide (counted from the N-terminus of the serpin-finger polypeptide) is glutamic acid.

In one embodiment the serpin-finger polypeptide consists of 8 to 14 amino acid residues, in one embodiment of 10 to 14 amino acid residues, and in one embodiment of 11 to 13 amino acid residues.

In one embodiment the further polypeptide is selected from immunoglobulins, immunoglobulin fragments, hormones, cytokines, growth factors, receptor ligands, receptor agonists, receptor antagonists, enzyme ligands, enzyme agonists, enzyme antagonists, cytotoxic agents, antiviral agents, imaging agents, and enzyme activity modulators.

Herein is reported as an aspect a fusion polypeptide comprising in N- to C-terminal direction a serpin-finger polypeptide fused to a biologically active polypeptide, optionally with a peptidic linker polypeptide in between.

In one embodiment the biologically active polypeptide is an antiviral agent.

In one embodiment the antiviral agent is an HIV fusion inhibitor polypeptide. In one embodiment the amino acid sequence of the HIV fusion inhibitor polypeptide is MTW-MEWDREINNYTSLIHSLIEESQN-QQEKNEQELLELDKWASLWNWF (SEQ ID NO: 13).

Another aspect as reported herein is a protein complex of a serpin-finger fusion polypeptide as reported herein and a serpin or a fragment thereof, wherein the fusion polypeptide is incorporated into the middle of beta-sheet A of the serpin as strand 4a.

Another aspect as reported herein is a pharmaceutical composition comprising the serpin-finger fusion polypeptide as reported herein or the protein complex as reported herein and optionally a pharmaceutically acceptable carrier. In one embodiment the pharmaceutical composition further comprises an additional therapeutic agent.

Also an aspect as reported herein is the serpin-finger fusion polypeptide as reported herein or the protein complex as reported herein for use as a medicament.

Another aspect as reported herein the serpin-finger fusion polypeptide as reported herein or the protein complex as reported herein is for use in treating a viral infection.

In one aspect as reported herein the serpin-finger fusion polypeptide as reported herein or the protein complex as reported herein is for use in inhibiting cell-cell-membrane fusion or in inhibiting the infection of a cell by a virus. In one embodiment the infection of a cell by a virus is an HIV infection and the serpin-finger fusion polypeptide is a serpin-finger HIV fusion inhibitor polypeptide fusion polypeptide.

One aspect as reported herein is the use of the serpin-finger fusion polypeptide as reported herein or the protein complex as reported herein in the manufacture of a medicament. In one embodiment the medicament is for treatment of a viral infection. In another embodiment the medicament is for inhibiting cell-cell-membrane fusion or for inhibiting the infection of a cell by a virus. In one embodiment the viral infection is an HIV infection and the serpin-finger fusion polypeptide is a serpin-finger HIV fusion inhibitor polypeptide fusion polypeptide.

Also an aspect as reported herein is a method of treating an individual having a viral infection comprising administering to the individual an effective amount of the serpin-finger fusion polypeptide as reported herein or the protein complex as reported herein. In one embodiment the viral infection is an HIV infection and the serpin-finger fusion polypeptide is a serpin-finger HIV fusion inhibitor polypeptide fusion polypeptide.

A further aspect as reported herein is a method of inhibiting cell-cell-membrane fusion, or a method of inhibiting the infection of a cell by a virus in an individual comprising administering to the individual an effective amount of the serpin-finger fusion polypeptide as reported herein or the protein complex as reported herein to inhibit cell-cell-membrane fusion or to inhibit the infection of a cell by a virus.

Another aspect as reported herein is a mixture comprising a serpin-finger fusion polypeptide as reported herein and a serpin or a fragment thereof, a pharmaceutical composition comprising this mixture and the use thereof as a medicament.

One aspect as reported herein is the use of a serpin or a fragment thereof for the manufacture of a protein complex with a serpin-finger fusion polypeptide comprising in N- to C-terminal direction a serpin-finger polypeptide fused to a biologically active polypeptide.

Another aspect as reported herein is a kit comprising the serpin-finger fusion polypeptide and a serpin in separate containers, optionally a further container for mixing these two components and also optionally an instruction sheet. In one embodiment the kit further comprises a means for detecting the fusion polypeptide in a sample.

DETAILED DESCRIPTION OF THE INVENTION

Herein is reported a serpin-finger fusion polypeptide comprising
a serpin-finger polypeptide, and
a further polypeptide,
wherein the further polypeptide can be any polypeptide exerting a biological activity, such as inhibition, activation, binding or labeling.

In one aspect herein a protein complex comprising a serpin-finger fusion polypeptide and a serpin is reported, wherein the fusion polypeptide is incorporated into the middle of beta-sheet A as strand 4a of the serpin.

The serpin-finger fusion polypeptide targets and anchors the fused further polypeptide with high affinity and functional spatial orientation to the serpin.

In one embodiment a serpin-finger fusion polypeptide comprising a serpin-finger polypeptide fused to an HIV fusion inhibitor polypeptide via a peptidic linker polypeptide is reported.

The term "serpin-finger polypeptide" as used within the current invention denotes a polypeptide that consists of 8 to 16 amino acid residues derived either from the natural reactive center loop of a serpin or from a synthetic analogue thereof. In one embodiment the amino acid sequence of the polypeptide consists of 11 to 13 amino acid residues. In one embodiment the amino acid sequence of the serpin-finger polypeptide is selected from AGAMFLEAIVM (SEQ ID NO: 01), AAGAMFLEAIVM (SEQ ID NO: 02), TEAAG-AMFLEAIVM (SEQ ID NO: 03), AGAMFLEAIVM (SEQ ID NO: 04), TEAAGAMFFEAIPM (SEQ ID NO: 05), TAV-VIA (SEQ ID NO: 06), SEAAASTAVVIA (SEQ ID NO: 07), TEAAGATAVVIA (SEQ ID NO: 08), TDAAGATAVVIA (SEQ ID NO: 09), SDAAGAMFLEAI (SEQ ID NO: 10), SEAAASMFLEAI (SEQ ID NO: 11), TIDEKGTEAAG-AMFLE (SEQ ID NO: 14), DVFEEGTEASAATAVK (SEQ ID NO: 15), DVDEAGTEAAAATTFA (SEQ ID NO: 16), QLNEEGVDTAGSTGVT (SEQ ID NO: 17), HIGEKGTEAAAVPEVE (SEQ ID NO: 18), EVDERGTEAVAGILSE (SEQ ID NO: 19), EVTEE-GVEAAAATAVV (SEQ ID NO: 20), EVTEEGAE-AAAATAVV (SEQ ID NO: 21), TVNEEGTQATTVTTVG (SEQ ID NO: 22), EVDENGTQAAAATGAV (SEQ ID NO: 23), EVNEEGTEAAAATAVV (SEQ ID NO: 24), DVNEE-GTEAAAGTGGV (SEQ ID NO: 25), EVNES-GTVASSSTAVI (SEQ ID NO: 26), DVFEE-GTEASAATAVK (SEQ ID NO: 27), EVTEEGTEATAATGSN (SEQ ID NO: 28), EITEDGGDS-IEVPGAR (SEQ ID NO: 29), ELSEVGVEAAAATSIA (SEQ ID NO: 30), ELTETGVEAAAASAIS (SEQ ID NO: 31), GTEAAGAMFLEAIPMS (SEQ ID NO: 82), and SGTEAAGAMFLEAIPMS (SEQ ID NO: 83). In one embodiment the amino acid sequence of the serpin-finger polypeptide is AGAMFLEAIVM (SEQ ID NO: 01), or AAG-AMFLEAIVM (SEQ ID NO: 02), or TEAAGAMFLEAIVM (SEQ ID NO: 03), or SEAAASTAVVIA (SEQ ID NO: 07), or SEAAASMFLEAI (SEQ ID NO: 11). In one embodiment the serpin-finger polypeptide is derived from alpha1-antitrypsin or antithrombin.

The term "serpin" denotes a superfamily of proteins with diverse functions. Exemplary members of the serpin superfamily are listed in the following. In one embodiment the serpin is selected from alpha1-antitrypsin (serpinA1), antitrypsin-related protein (serpinA2), alpha1-antichymotrypsin (serpinA3), kallistatin (serpinA4), protein C inhibitor (serpinA5), cortisol binding globulin (serpinA6), thyroxine-binding globulin (serpinA7), angiotensinogen (serpinA8), centerin (serpinA9), protein Z-related protease inhibitor (serpinA10), serpinA11, vaspin (serpinA12), serpinA13, monocyte neutrophils elastase inhibitor (serpinB1), plasminogen activator inhibitor-2 (serpinB2), squamous cell carcinoma antigen-1 and -2 (serpinB3 and B4), maspin (serpinB5), PI-6 (serpinB6), megsin (serpinB7), PI-8 (serpinB8), PI-9 (serpinB9), bomapin (serpinB10), serpinB11, yukopin (serpinB12), hurpin/headpin (serpinB13), antithrombin (serpinC1), heparin cofactor II (serpinD1), plasminogen activator inhibitor 1 (serpinE1), glia derived nexin/protease nexin I (serpinE2), pigment epithelium derived factor (serpinF1), alpha2-antiplasmin (serpinF2), complement 1-inhibitor (serpinG1), HSP47 (serpinH1), neuroserpin (serpinI1) and pancpin (serpinI2). A fragment of a serpin is a molecule that still exerts the function to incorporate a serpin-finger fusion polypeptide as reported herein into the middle of beta-sheet A as strand 4a of the serpin fragment.

The term "biologically active polypeptide" as used herein refers to an organic molecule, e.g. a biological macromolecule such as a peptide, protein, glycoprotein, nucleoprotein, mucoprotein, lipoprotein, synthetic polypeptide or protein, that causes a biological effect when administered in or to artificial biological systems, such as bioassays e.g. using cell lines and viruses, or in vivo to an animal, including but not limited to birds or mammals, including humans. This biological effect can be but is not limited to enzyme inhibition or activation, binding to a receptor or a ligand, either at the binding site or circumferential, signal triggering or signal modulation. Biologically active molecules are without limitation for example immunoglobulins, or hormones, or cytokines, or growth factors, or receptor ligands, or agonists or antagonists, or cytotoxic agents, or antiviral agents, or imaging agents, or enzyme inhibitors, enzyme activators or enzyme activity modulators such as allosteric substances. In a one embodiment the biologically active polypeptide is an immunoglobulin, immunoglobulin conjugate, or an HIV fusion inhibitor polypeptide.

A "HIV fusion inhibitor polypeptide" is a polypeptide which inhibits events associated with membrane fusion or the membrane fusion event itself, including, among other things, the inhibition of infection of uninfected cells by a HIV virus due to membrane fusion. The HIV fusion inhibitor polypeptide is in one embodiment a linear polypeptide. For example, it is as in one embodiment derived from the HIV gp41 ectodomain, e.g., such as DP107 or DP178. The amino acid sequence of the HIV fusion inhibitor polypeptide consists of 5 to 100 amino acid residues, in one embodiment of 10 to 75 amino acid residues, in a further embodiment of 15 to 50 amino acid residues. In one embodiment the amino acid sequence of the HIV fusion inhibitor polypeptide is selected from the group consisting of SEQ ID NO: 13 and SEQ ID NO: 32 to 42. Further examples of HIV fusion inhibitor polypeptides can be found in U.S. Pat. Nos. 5,464,933, 5,656,480, 6,013,263, 6,017,536, 6,020,459, 6,093,794, 6,060,065, 6,258,782, 6,348,568, 6,479,055, 6,656,906, WO 1996/19495, WO 1996/40191, WO 1999/59615, WO 2000/69902, and WO 2005/067960. For example, the amino acid sequences of the HIV fusion inhibitor polypeptide can be selected from the group comprising SEQ ID NO: 1 to 10 of U.S. Pat. No. 5,464,933; SEQ ID NO: 1 to 15 of U.S. Pat. No. 5,656,480; SEQ ID NO: 1 to 10 and 16 to 83 of U.S. Pat. No. 6,013,263; SEQ ID NO: 1 to 10, 20 to 83 and 139 to 149 of U.S. Pat. No. 6,017,536; SEQ ID NO: 1 to 10, 17 to 83 and 210 to 214 of U.S. Pat. No. 6,093,794; SEQ ID NO: 1 to 10, 16 to 83 and 210 to 211 of U.S. Pat. No. 6,060,065; SEQ ID NO: 1286 and 1310 of U.S. Pat. No. 6,258,782; SEQ ID NO: 1129, 1278-1309, 1311 and 1433 of U.S. Pat. No. 6,348,568; SEQ ID NO: 1 to 10 and 210 to 238 of U.S. Pat. No. 6,479,055; SEQ ID NO: 1 to 171, 173 to 216, 218 to 219, 222 to 228, 231, 233 to 366, 372 to 398, 400 to 456, 458 to 498, 500 to 570, 572 to 620, 622 to 651, 653 to 736, 739 to 785, 787 to 811, 813 to 823, 825, 827 to 863, 865 to 875, 877 to 883, 885, 887 to 890, 892 to 981, 986 to 999, 1001 to 1003, 1006 to 1018, 1022 to 1024, 1026 to 1028, 1030 to 1032, 1037 to 1076, 1078 to 1079, 1082 to 1117, 1120 to 1176, 1179 to 1213, 1218 to 1223, 1227 to 1237, 1244 to 1245, 1256 to 1268, 1271 to 1275, 1277, 1345 to 1348, 1350 to 1362, 1364, 1366, 1368, 1370, 1372, 1374 to 1376, 1378 to 1379, 1381 to 1385, 1412 to 1417, 1421 to 1426, 1428 to 1430, 1432, 1439 to 1542, 1670 to 1682, 1684 to 1709, 1712 to 1719, 1721 to 1753, 1755 to 1757 of U.S. Pat. No. 6,656,906; or SEQ ID NO: 5 to 95 of WO 2005/067960.

TABLE 1

HIV fusion inhibitor polypeptide amino acid sequences.

| | | SEQ ID NO: |
|---|---|---|
| DP-107 | NNLLRAIEAQQHLLQLTVWGIKQLQARILAVERYLKDQ | 32 |
| DP-178 | QQEKNEQDLLALDKWASLWTWFDISHWLWYIKIFIMIV | 33 |
| C-34 | WMEWDREINNYTSLIHSLIEESQNQQEKNEQELL | 34 |
| N-36 | SGIVQQQNNLLRAIEAQQHLLQLTVWGIKQLQARIL | 35 |
| T-20 | YTSLIHSLIEESQNQQEKNEQELLELDKWASLWNWF | 36 |
| T-651 | MTWMEWDREINNYTSLIHSLIEESQNQQEKNEQELL | Residues 1-36 of SEQ ID NO: 13 |

TABLE 1-continued

HIV fusion inhibitor polypeptide amino acid sequences.

| | | SEQ ID NO: |
|---|---|---|
| T-1249 | WQEWEQKITALLEQAQIQQEKNEYELQKLDKWASLWEWF | 37 |
| T-1357 | WQEWEQKITALLEQAQIQQEKNEYELQKLDKWASLWEWF | 38 |
| T-1357 variant | MRGSHHHHHHAIDVIEGRWQEWEQKITALLEQAQIQQEKN EYELQKLDKWASLWEWFG | 39 |
| T-2635 | TTWEAWDRAIAEYAARIEALIRAAQEQQEKNEAALREL | 40 |
| HIV-1 gp41 ectodomain variant single mutant: I568P | VQARQLLSGIVQQQNNLLRAIEGQQHLLQLTVWGPKQLQA RILAVERYLKDQQLLGIWGCSGKLICTTAVPWNASWSNKS LEQIWNNMTWMEWDREINNYTSLIHSLIEESQNQQEKNEQ ELL | 41 |
| HIV-1 gp41 ectodomain variant quadruple mutant: I568P, L550E, L566E, I580E | MGAASMTLTVQARQLLSGIVQQQNNELRAIEGQQHLEQLT VWGPKQLQARELAVERYLKDQQLLGIWGCSGKLICTTAVP WNASWSNKSLEQIWNNMTWMEWDREINNYTSLIHSLIEES QNQQEKNEQELL | 42 |

The term "peptidic linker polypeptide" as used within this application denotes a peptidic linker polypeptide of natural and/or synthetic origin. It consists of a linear amino acid residue chain in which the 20 naturally occurring amino acids are the monomeric building blocks. The chain has a length of 1 to 50 amino acid residues, in one embodiment of 1 to 28 amino acid residues, in another embodiment of 3 to 25 amino acid residues. The peptidic linker polypeptide may contain repetitive amino acid sequences or sequences of naturally occurring polypeptides, such as polypeptides with a hinge-function. The peptidic linker polypeptide has the function to ensure that a polypeptide in a conjugate or fusion each of the conjugated/fused polypeptides can perform its biological activity by allowing each of the polypeptides to fold correctly and to be presented properly. In one embodiment the peptidic linker polypeptide is a "synthetic peptidic linker polypeptide" that is designated to be rich in glycine, glutamine, and/or serine residues. The residues are arranged e.g. in small repetitive units of up to five amino acid residues, such as GGGGS (SEQ ID NO: 90), GGGSG (SEQ ID NO: 91), GGSGG (SEQ ID NO: 12), GSGGG (SEQ ID NO: 92), QQQQG (SEQ ID NO: 93), or SSSSG (SEQ ID NO: 94). The repetitive unit may be repeated for two to five times to form a multimeric unit. At the amino- and/or carboxy-terminal ends of the multimeric unit up to six additional arbitrary, naturally occurring amino acid residues may be added. Other synthetic peptidic linker polypeptides are composed of a single amino acid residue, that is repeated of from 10 to 20 times and which may comprise at the amino- and/or carboxy-terminal end up to six additional arbitrary, naturally occurring amino acid residues, such as e.g. serine in the linker GSSSSSSSSSSSSSSSG (SEQ ID NO: 61). In one embodiment the peptidic linker polypeptide is selected from antibody hinge region, LSL-SPGK (SEQ ID NO: 43), LSPNRGEC (SEQ ID NO: 44), [GQ$_4$]$_3$GNN (SEQ ID NO: 47), LSLSGG (SEQ ID NO: 69), LSLSPGG (SEQ ID NO: 70), G$_3$[SG$_4$]$_2$SG (SEQ ID NO: 73), G$_3$[SG$_4$]$_2$SG$_2$ (SEQ ID NO: 74) or STT (SEQ ID NO: 75). All peptidic linker polypeptides can be encoded by a nucleic acid molecule and therefore can be recombinantly expressed. As the peptidic linker polypeptides are themselves polypeptides, the serpin-finger polypeptide is connected to the peptidic linker polypeptide via a peptide bond that is formed between two amino acids.

TABLE 2

Peptidic linker polypeptide amino acid sequences.

| No. | Linker peptides | SEQ ID NO: |
|---|---|---|
| 1 | G$_2$SG$_2$ | 12 |
| 2 | LSLSPGK | 43 |
| 3 | LSPNRGEC | 44 |
| 4 | [GQ$_4$]$_3$ | 45 |
| 5 | [GQ$_4$]$_3$G | 46 |
| 6 | [GQ$_4$]$_3$GNN | 47 |
| 7 | GGG[SG$_4$]$_2$SGG | 48 |
| 8 | GGG[SG$_4$]$_2$SGN | 49 |
| 9 | [SG$_4$]$_3$ | 50 |
| 10 | [SG$_4$]$_3$G | 51 |
| 11 | [SG$_4$]$_3$T | 52 |
| 12 | [SG$_4$]$_3$GG | 53 |
| 13 | [SG$_4$]$_3$GGT | 54 |
| 14 | [SG$_4$]$_3$GGN | 55 |
| 15 | [SG$_4$]$_3$GAS | 56 |

TABLE 2-continued

Peptidic linker polypeptide amino acid sequences.

| No. | Linker peptides | SEQ ID NO: |
|---|---|---|
| 16 | [SG$_4$]$_5$ | 57 |
| 17 | [SG$_4$]$_5$G | 58 |
| 18 | [SG$_4$]$_5$GG | 59 |
| 19 | [SG$_4$]$_5$GAS | 60 |
| 20 | G(S)$_{15}$G | 61 |
| 21 | G(S)$_{15}$GAS | 62 |
| 22 | G | |
| 23 | N | |
| 24 | GST | 63 |
| 25 | [G$_4$S]$_3$GAS | 64 |
| 26 | [G$_4$S]$_3$G | 65 |
| 27 | [G$_4$S]$_5$G | 66 |
| 28 | [G$_4$S]$_3$GG | 67 |
| 29 | [G$_4$S]$_5$GG | 68 |
| 30 | LSLSGG | 69 |
| 31 | LSLSPGG | 70 |
| 32 | [G$_3$S]$_5$ | 71 |
| 33 | [G$_3$S]$_5$GGG | 72 |
| 34 | G$_3$[SG$_4$]$_2$SG | 73 |
| 35 | G$_3$[SG$_4$]$_2$SG$_2$ | 74 |
| 36 | STT | 75 |

The term "into the middle of beta-sheet A as strand 4a" denotes the insertion of a serpin-finger fusion polypeptide between strands 4 and 5 of beta-sheet A of a serpin, e.g. beta-sheet A of alpha1-antitrypsin, or antithrombin.

In a fusion polypeptide comprising a serpin-finger polypeptide fused to a polypeptide with biological activity (optionally via a peptidic linker) the fused polypeptide with biological activity has improved properties compared to the isolated polypeptide. The fusion polypeptide can e.g. be inserted into the beta-sheet A of a serpin, such as alpha1-antitrypsin, to improve the in vivo half-life of the fused polypeptide with biological activity. It has been found that a serpin-finger polypeptide derived from antithrombin inserts well into the beta sheets of alpha1-antitrypsin. This combination is one embodiment of the aspects of the invention. This can e.g. be seen from the in vitro association data presented in Table 3.

In addition it has been found that not the serpin-finger polypeptide with the shortest amino acid sequence of six amino acid residues inserts fastest but a longer one of 11 to 13 amino acid residues length does. Furthermore the amino acid glutamic acid as second amino acid of the serpin-finger polypeptide (counted from the N-terminus of the serpin-finger polypeptide) increases the insertion efficiency of the serpin-finger fusion polypeptide into the serpin beta sheet.

TABLE 3

Serpin-finger polypeptide amino acid sequence and in vitro association $T_{1/2}$ with the serpin alpha1-antitrypsin.

| serpin-finger polypeptide amino acid sequence | in vitro association $T_{1/2}$ [h] |
|---|---|
| Ac-TEAAGAMFLEAIVM (SEQ ID NO: 3) | 10 |
| Ac-AGAMFLEAIVM (SEQ ID NO: 4) | 4-5 days |
| Ac-TEAAGAMFFEAIPM (SEQ ID NO: 5) | 10 |
| Ac-TAVVIA (SEQ ID NO: 6) | 16 |
| Ac-SEAAASTAVVIA (SEQ ID NO: 7) | 1.4 |
| Ac-TEAAGATAVVIA (SEQ ID NO: 8) | 9.5 |
| Ac-TDAAGATAVVIA (SEQ ID NO: 9) | 16 |
| Ac-SDAAGAMFLEAI (SEQ ID NO: 10) | 16 |
| Ac-SEAAASMFLEAI (SEQ ID NO: 11) | 4 |

In the following the aspects as reported herein are exemplified with a serpin-finger fusion polypeptide comprising a peptidic linker polypeptide and an HIV fusion inhibitor polypeptide as biologically active polypeptide. The following is presented solely to exemplify the herein reported subject matter and has not to be treated as limitation or restriction.

Different fusion polypeptides have been prepared. The encoding genes have been obtained by chemical gene synthesis and the polypeptides have been recombinantly produced in E. coli. The different fusion polypeptides have been expressed as a construct comprising a streptavidin carrier protein as purification tag, a trypsin cleavage site, a serpin-finger polypeptide, a peptidic linker polypeptide, and a HIV fusion inhibitor polypeptide.

In one embodiment the amino acid sequence of the trypsin cleavage site is GR.

The amino acid sequence of the serpin-finger polypeptide is in one embodiment SEAAASTAVVIA (SEQ ID NO: 07) either with or without N-terminal and/or C-terminal linker whereby the linker is independently and individually selected from S, or G, or SG.

The amino acid sequence of the peptidic linker polypeptide is in one embodiment [SG$_4$]$_3$ (SEQ ID NO: 50), or [SG$_4$]$_3$T (SEQ ID NO: 52), or STT (SEQ ID NO: 75).

The amino acid sequence of fusion polypeptide FP-1 is SEQ ID NO: 76, the amino acid sequence of fusion polypeptide FP-2 is SEQ ID NO: 77, and the amino acid sequence of fusion polypeptide FP-3 is SEQ ID NO: 78. In the fusion polypeptides FP-1 to FP-3 the same serpin-finger polypeptide is conjugated to different HIV fusion inhibitor polypeptides. The fusion polypeptide FP-3 is expressed better in E. coli than FP-2 and in turn FP-2 is expressed better than the fusion polypeptide FP-1. The same sequence of the fusion polypeptides is obtained for the binding to target HIV HR-1 polypeptide (FP-3>FP-2>FP-1) in a BIAcore assay. The same sequence has also been found for the anti-viral activity in a cell-cell-fusion-assay (CCF-assay).

By gel-electrophoresis (urea-PAGE) it has been shown that a protein complex of the fusion polypeptide according to the invention and alpha1-antitrypsin is formed. The stable complex formation between the individual FP-X fusion polypeptides and alpha1-antitrypsin is shown in FIG. 1.

As the protein complex and free alpha1-antitrypsin cannot be separated by SDS-PAGE gel electrophoresis a determination of the formation of the protein complex by Western blot with incubation with a HR1-polypeptide-biotin-conjugate has to be performed. An exemplary blot is shown in FIG. 2. For preparative separation of free fusion polypeptide and the protein complex size exclusion chromatography can be employed. An exemplary chromatogram with SDS-PAGE analysis of individual fractions is shown in FIG. 3.

Different serpin-finger fusion polypeptides have been assayed for their association rate with the serpin alpha1-antitrypsin. The fastest binders have an in vitro association T1/2 of from 1 to 4 hours.

In Table 4 the binding characteristics of the FP-1 to FP-3 fusion polypeptides compared to the isolated HIV fusion inhibitor polypeptide is shown.

TABLE 4

Binding properties of FP-1 to FP-3 to HIV HR1 polypeptide.

| Peptide | $k_a$ (1/Ms) | $k_d$ (1/s) | $K_A$ (1/M) | $K_D$ (M) | HIV fusion inhibitor polypeptide |
|---|---|---|---|---|---|
| T-1249 | 1.24e6 | 1.27e−3 | 9.80e08 | 1.02e−09 | |
| T-651 | 1.65e6 | 1.41e−4 | 1.17e10 | 8.55e−11 | |
| T-2635 | 1.11e6 | 7.38e−5 | 1.50e10 | 6.65e−11 | |
| FP-1 | 2.27e5 | 3.61e−4 | 6.29e08 | 1.59e−09 | T-1249 |
| FP-2 | 1.29e6 | 1.19e−4 | 1.08e10 | 9.24e−11 | T-651 |
| FP-3 | 9.91e5 | 3.07e−5 | 3.22e10 | 3.10e−11 | T-2635 |

The binding affinity determined by surface plasmon resonance displays similar binding constants for the free fusion inhibitor and the three fusion peptides. From the BIAcore binding diagrams shown in FIG. 4 it can be seen on the one hand that the protein complex is binding to the HIV HR1 polypeptide (FIG. 4b) and on the other hand that the FP-2 containing protein complex has the best affinity of the three complexes for the immobilized HR1 polypeptide.

From the Table 5 it can be seen that the fusion polypeptides FP-1 to FP-3 have comparable antiviral activity as the isolated HIV fusion inhibitor polypeptides.

TABLE 5

Antiviral activity of fusion polypeptides in a CCF-assay.

| HIV fusion inhibitor polypeptide | IC$_{50}$ [nM] | fusion polypeptide | IC$_{50}$ [nM] |
|---|---|---|---|
| T-1249 | 60 | FP-1 | 700 |
| T-651 | 500 | FP-2 | 330 |
| T-2635 | 140 | FP-3 | 200 |

The following examples, sequence listing and figures are provided to aid the understanding of the present invention, the true scope of which is set forth in the appended claims. It is understood that modifications can be made in the procedures set forth without departing from the spirit of the invention.

In some embodiments, the invention relates to:
1. A fusion polypeptide comprising a serpin-finger polypeptide and a biologically active polypeptide.
2. The fusion polypeptide according to claim 1, characterized in the amino acid residue at amino acid position 2 of the serpin-finger polypeptide is glutamic acid.
3. The fusion polypeptide according claim 1, characterized in that the serpin-finger polypeptide has an amino acid sequence of a length of 8 to 14 amino acid residues.
4. The fusion polypeptide according to any one of the preceding claims, characterized in that the biologically active polypeptide is an HIV fusion inhibitor polypeptide.
5. The fusion polypeptide according to any one of the preceding claims, characterized in that the amino acid sequence of the serpin-finger polypeptide is selected from TEAAGAMFLEAIVM (SEQ ID NO: 03), TEAAGAMFFEAIPM (SEQ ID NO: 05), SEAAASTAVVIA (SEQ ID NO: 07), TEAAGATAVVIA (SEQ ID NO: 08), or SEAAASMFLEAI (SEQ ID NO: 11).
6. The fusion polypeptide according to claim 5, characterized in that the amino acid sequence of the serpin-finger polypeptide is SEAAASTAVVIA (SEQ ID NO: 07), or SEAAASMFLEAI (SEQ ID NO: 11).
7. The fusion polypeptide according to any one of the preceding claims, characterized in that the fusion polypeptide comprises a peptidic linker polypeptide between the serpin-finger polypeptide and the biologically active polypeptide with the amino acid sequence of GGSGG (SEQ ID NO: 12).
8. The fusion polypeptide according to any one of claims 4 to 7, characterized in that the amino acid sequence of the HIV fusion inhibitor polypeptide is MTWMEWDREINNYTSLIHSLIEESQNQQEKNEQELLELDKWASLWN WF (SEQ ID NO: 13).
9. A protein complex of a fusion polypeptide according to any one of claims 1 to 8 and a serpin.
10. The protein complex according to claim 9, characterized in that the serpin is selected from alpha1-antitrypsin and antithrombin.
11. A fusion polypeptide according to any one of claims 1 to 8 or a protein complex according to any one of claim 9 or 10 for use as a medicament.
12. A fusion polypeptide according to any one of claims 1 to 8 or a protein complex according to any one of claim 9 or 10 for use in the treatment of a virus infection.
13. A fusion polypeptide according to any one of claims 4 to 8 or a protein complex according to any one of claim 9 or 10 for use in the treatment of an HIV infection.
14. Use of alpha1-antitrypsin or antithrombin for the manufacture of a protein complex with a fusion polypeptide according to any one of claims 1 to 8.
15. A kit comprising
  a fusion polypeptide according to any one of claims 1 to 8, or a protein complex according to any one of claim 9 or 10, and
  alpha1-antitrypsin or antithrombin.

| DESCRIPTION OF THE SEQUENCE LISTING | |
|---|---|
| SEQ ID NO: 1 to 11, 14 to 31, 82, 83 | serpin-finger polypeptide amino acid sequences |
| SEQ ID NO: 12 and 43 to 75 | peptidic linker polypeptide amino acid sequences |
| SEQ ID NO: 13 and 32 to 42 | HIV fusion inhibitor polypeptide amino acid sequences |
| SEQ ID NO: 76 | fusion polypeptide 1 amino acid sequence |
| SEQ ID NO: 77 | fusion polypeptide 2 amino acid sequence |
| SEQ ID NO: 78 | fusion polypeptide 3 amino acid sequence |
| SEQ ID NO: 79 and 80 | primer sequences |
| SEQ ID NO: 81 | core streptavidin amino acid sequence |
| SEQ ID NO: 84 to 86 | FP-1, FP-2, FP-3 encoding nucleic acid |
| SEQ ID NO: 87 | HIV HR1 amino acid sequence |

BRIEF DESCRIPTION OF THE DRAWINGS

(FIG. 4A); and BIAcore diagram showing the binding of FP-2 and FP-3 containing protein complex to immobilized HIV HR1 polypeptide (FIG. 4B).

EXAMPLES

Figure 1:
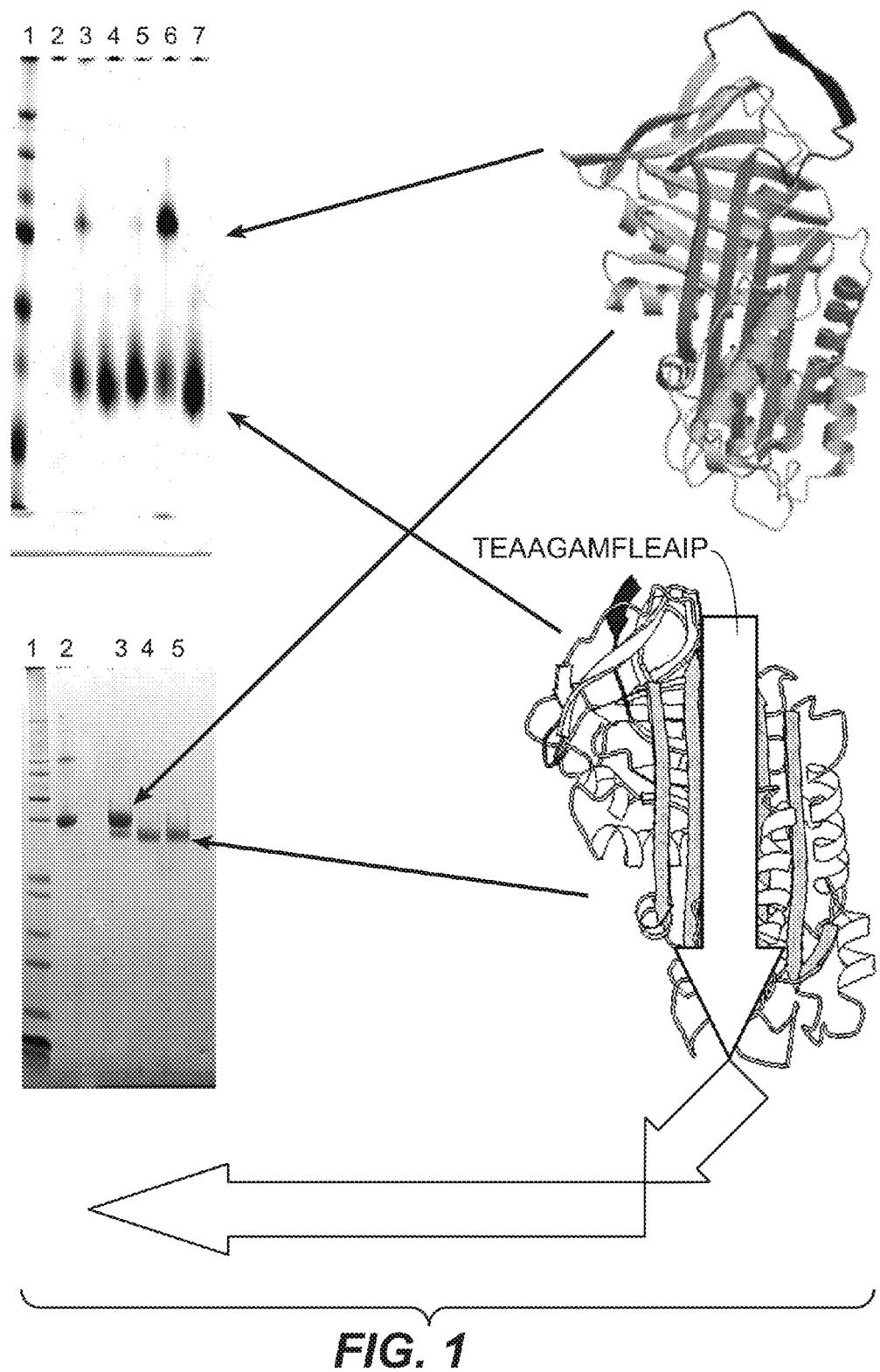
FIG. 1 Analysis of the protein complex formation of the fusion polypeptide and alpha1-antitrypsin. The upper image shows 8 M urea PAGE-SDS gel after one week incubation at 37° C. [lane 1-molecular weight marker; lane 3-(FP-1)-AAT; lane 4-(FP-2)-AAT; lane 5-(FP-3)-AAT; lane 6-(FP-1)-AAT; lane 7-(FP-2)-AAT). The lower image shows a 12% SDS-PAGE of a gel-filtration separation of the incubation (lane 1-molecular weight marker; lane 2-AAT; lane 3-(FP-1)-AAT; lane 4-(FP-2)-AAT; lane 5-(FP-3)-AAT). [AAT=alpha1-antitrypsin]("TEAAGAMFLEAIP" disclosed as SEQ ID NO: 88)
Figure 2:
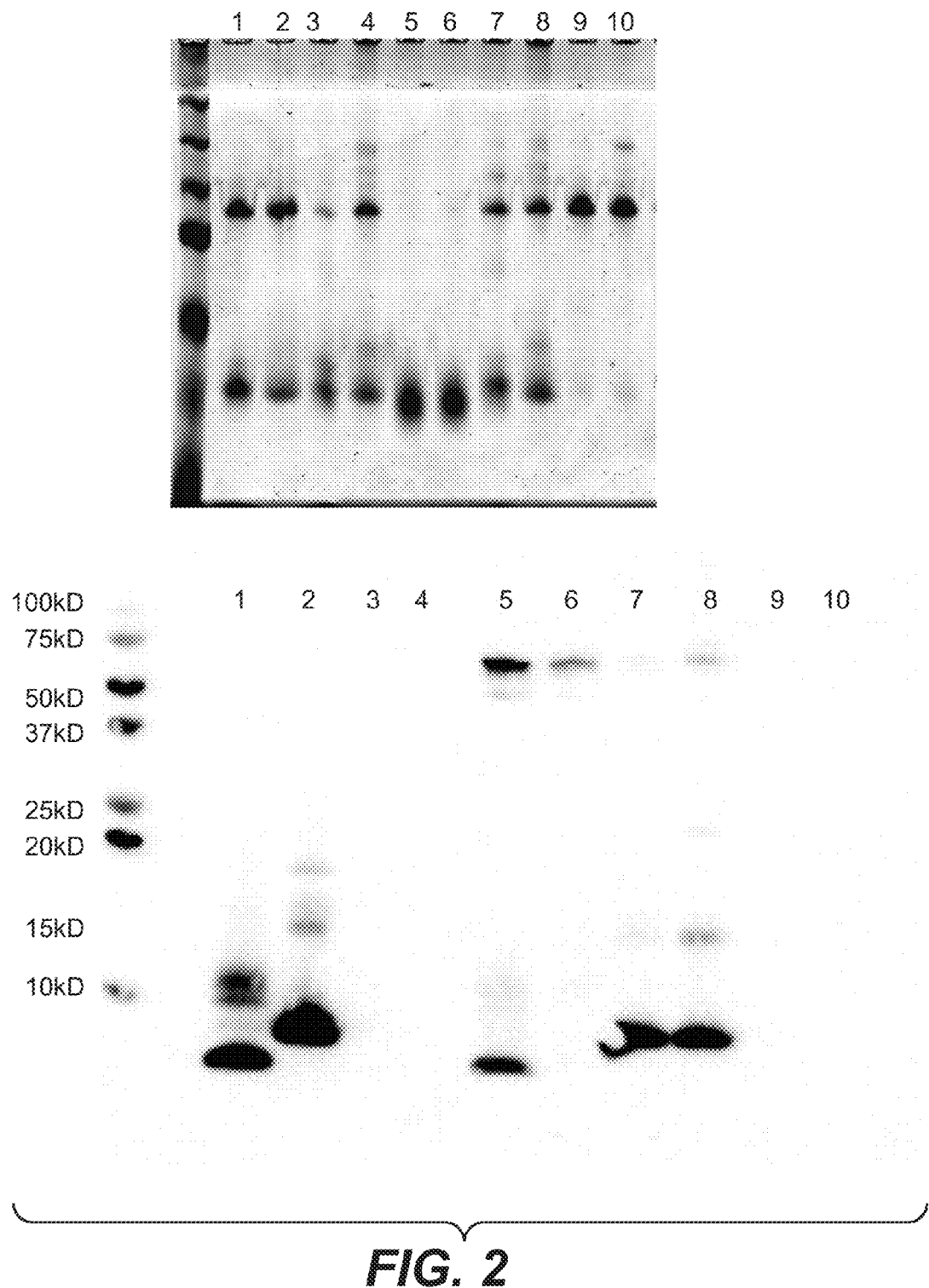
FIG. 2 The upper image shows 8 M urea PAGE-SDS gel with a 4 day incubation of the following molecules at the designated temperatures. Lane 1=FP-2 (37° C.); lane 2=FP-3 (37° C.); lane 3=FP-2 (45° C.); lane 4=FP-3 (45° C.); lane 5=FP-2+chaperon (37° C.); lane 6=FP-3+chaperon (37° C.); lane 7=FP-2 (45° C.); lane 8=FP-3 (45° C.); lane 9=AAT (37° C.), control; lane 10=ATT (45° C.), control. The lower images shows a Western blot using a HR1 probe. Lane 1=FP-2; lane 2=FP-3; lane 3=AAT (45° C.); lane 4=AAT (room temperature); lane 5=protein complex (AAT+FP-2) (37° C.); lane 6=protein complex (AAT+FP-2) (45° C.) purified by SEC; lane 7=protein complex (AAT+FP-3) (37° C.); lane 8=protein complex (AAT+FP-3) (45° C.; lane 9=protein complex (AAT+FP-2)+gel-filtration+chaperone; 10=protein complex (AAT+FP-3)+SEC purification)+chaperone. The chaperon (HSP70) facilitates formation of the latent conformation.
Figure 3:
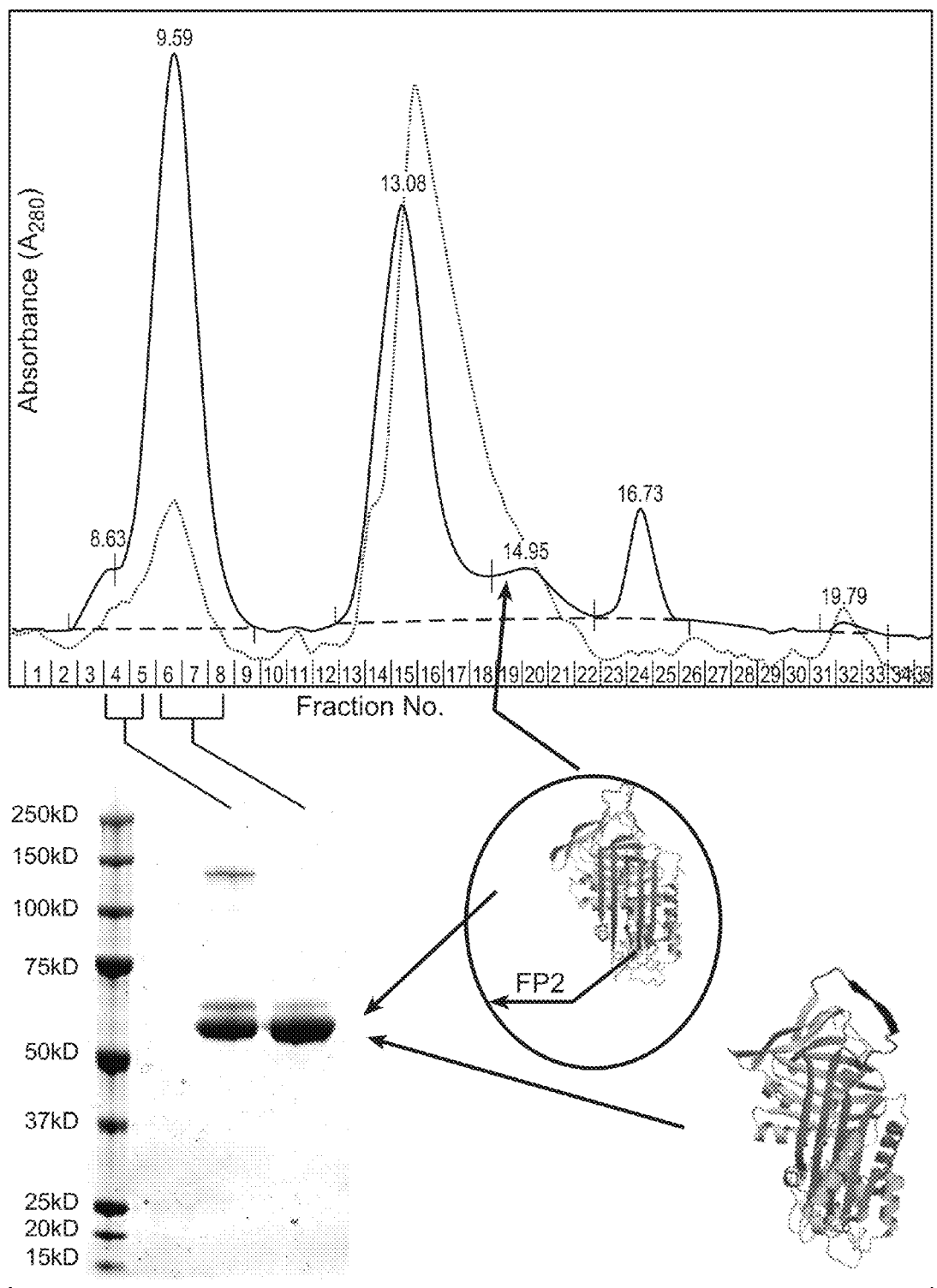
FIG. 3 Exemplary size exclusion chromatogram (upper image) and gel filtration separation (lower image) of free fusion polypeptide (FP-2) and protein complex (ATT+FP-2).
Figure 4A:
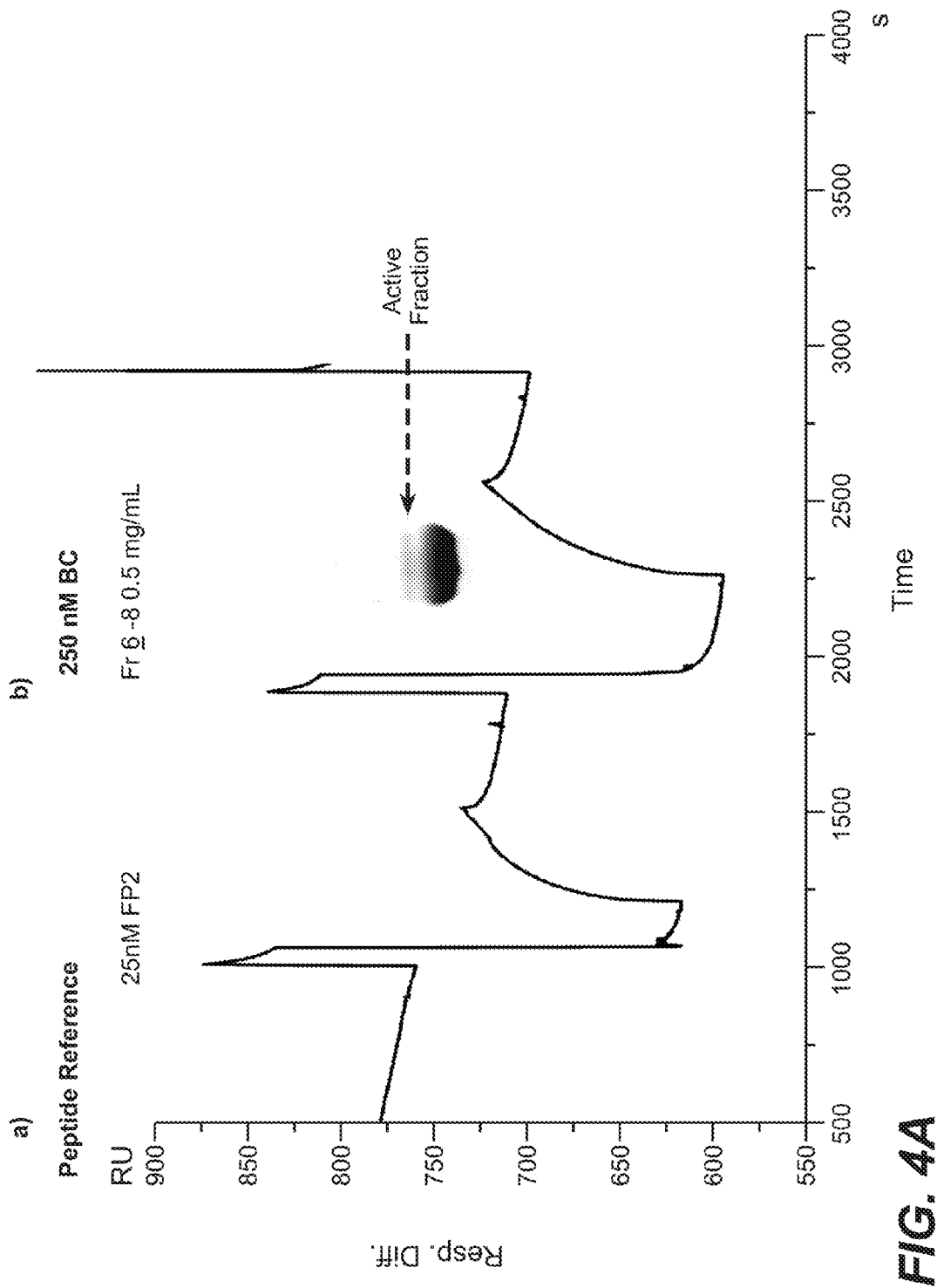
FIGS. 4A and 4B BIAcore diagram showing the binding of free FP-2 and protein complex of FP-2 and alpha1-antitrypsin to immobilized HIV HR1 polypeptide.
Figure 4B:
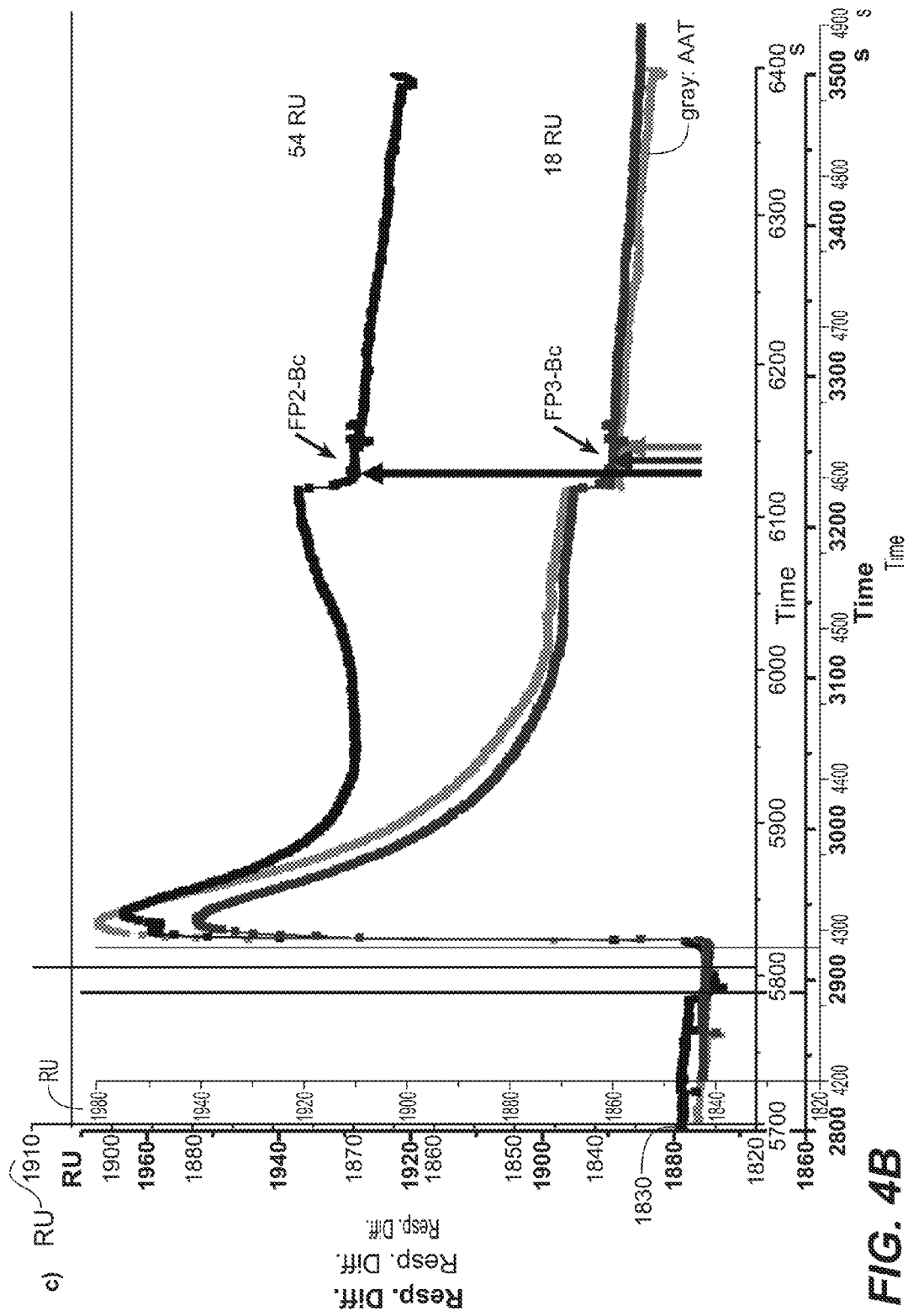

Materials & Methods
Recombinant DNA techniques

Standard methods were used to manipulate DNA as described in Sambrook, J., et al., Molecular Cloning: A Laboratory Manual; Cold Spring Harbor Laboratory Press, Cold Spring Harbor, N.Y. (1989). The molecular biological reagents were used according to the manufacturer's instructions.
Gene Synthesis Desired gene segments were prepared by chemical synthesis. Desired gene segments were prepared by gene synthesis. The synthesized gene fragments were cloned into a specified expression vector. The DNA sequence of the subcloned gene fragments were confirmed by DNA sequencing.
Protein Determination The protein concentration of the conjugate was determined by determining the optical density (OD) at 280 nm, using the molar extinction coefficient calculated on the basis of the amino acid sequence.

Example 1

Making of the Expression Plasmids

The fusion polypeptides FP-1, FP-2 and FP-3 were prepared by recombinant means. They were expressed as a larger fusion protein in *E. coli* using core-streptavidin as a carrier protein for high level expression in *E. coli*. The desired polypeptides were released by enzymatic cleavage in vitro using either trypsin (FP-1 and FP-2) or the endoproteinase LysC (FP-3).
Design of the Core-streptavidin Carrier Fusion Proteins The polypeptides FP-1 (SEQ ID NO: 76=GR+SEQ ID NO: 05+SEQ ID NO: 52+SEQ ID NO: 37), FP-2 (SEQ ID NO: 77=GR+SEQ ID NO: 82+SEQ ID NO: 75+SEQ ID NO: 13) and FP-3 (SEQ ID NO: 78=GR+SEQ ID NO: 83+SEQ ID NO: 50+SEQ ID NO: 40) were fused to the core-streptavidin sequence (SEQ ID NO: 81) via a GR or GK protease linker containing a unique trypsin or LysC endoproteinase cleavage site, respectively.

The core-streptavidin fusion genes comprising the core-streptavidin encoding nucleic acid, the short endoproteinase linker encoding nucleic acid (GR), the serpin-finger polypeptide encoding nucleic acid, the linker encoding nucleic acid and the HIV fusion inhibitor peptide encoding nucleic acid were assembled with known recombinant methods and techniques by connection of the according nucleic acid segments. The nucleic acid sequences encoding the polypeptides F1, F2 and F3 were made by chemical synthesis and then ligated into an *E. coli* plasmid for amplification. The subcloned nucleic acid sequences were verified by DNA sequencing.
Making and Description of the Basic/Starting *E. coli* Expression Plasmid 4980

Plasmid 4980 (4980-pBRori-URA3-LACI-SAC) is an expression plasmid for the expression of core-streptavidin in *E. coli*. It was generated by ligation of the 3142 bp long EcoRI/CelII-fragment derived from plasmid 1966 (1966-pBRori-URA3-LACI-T-repeat; reported in EP-B 1 422 237) with the 435 bp long core-streptavidin encoding EcoRI/CelII-fragment.

The core-streptavidin *E. coli* expression plasmid comprises the following elements:
- the origin of replication from the vector pBR322 for replication in *E. coli* (corresponding to by position 2517-3160 according to Sutcliffe, G., et al., Quant. Biol. 43 (1979) 77-90),
- the URA3 gene of *Saccharomyces cerevisiae* coding for orotidine 5'-phosphate decarboxylase (Rose, M., et al., Gene 29 (1984) 113-124) which allows plasmid selection by complementation of *E. coli* pyrF mutant strains (uracil auxotrophy),
- the core-streptavidin expression cassette built up of
  - the T5 hybrid promoter (T5-PN25/03/04 hybrid promoter according to Bujard, H., et al., Methods. Enzymol. 155 (1987) 416-433 and Stueber, D., et al., Immunol. Methods IV (1990) 121-152) including a synthetic ribosomal binding site according to Stueber, D., et al. (see before),
  - the core-streptavidin gene, and
  - two bacteriophage-derived transcription terminators, the λ-T0 terminator (Schwarz, E., et al., Nature 272 (1978) 410-414) and the fd-terminator (Beck, E., and Zink, B., Gene 1-3 (1981) 35-58), and
- the lad repressor gene from *E. coli* (Farabaugh, P. J., Nature 274 (1978) 765-769).

Making of the FP-1, FP-2, and FP-3 Fusion Polypeptide Expression Plasmids
a) Plasmid 4981

Plasmid 4981 (4981-SAC-Serpin1-T1249) is the plasmid for the expression of core-streptavidin-FP-1 protein in *E. coli*. It was prepared by insertion of the following 232 bp long NheI/CelII-F1 gene segment (encoding the F1 polypeptide SEQ ID NO: 84)

```
  1 gctagcggtc gtaccgaagc cgcgggcgct atgttcctgg 41 aagcaatccc gatgtccgga ggtggcggtt ctggtggcgg 81 tggttccggc ggtggtggca cgtggcagga atgggaacag 121 aaaatcaccg ctcttctaga acaggcgcag atccagcagg 161 agaaaaacga atacgaactg cagaagcttg acaaatgggc 201 ttctctgtgg gaatggttct aatgagctga gc
``` into the 3547 bp long NheI/CelII-4980 plasmid fragment.

b) Plasmid 4982

Plasmid 4982 (4982-SAC-Serpin2-T651) is the plasmid for the expression of core-streptavidin-FP-2 protein in *E. coli*. It was prepared by insertion of the following 181 bp long NheI/CelII-F2 gene segment (encoding the F2 polypeptide SEQ ID NO: 85)

```
  1 gctagcggtc gtggcactga agctgcaggt gcgatgtttc 41 tagaagctat cccgatgtcc accacgtgga tggagtggga 81 caaagaaatc aacaactaca caagcttgat ccactccctg 121 atcgaagaat cccagaacca gcaggagaaa aacgaacagg 161 aactgctgta atgagctgag c
``` into the 3547 bp long NheI/CelII-4980 plasmid fragment.

c) Plasmid 4983

Plasmid 4983 (4983-SAC-Serpin3-T2635) is the plasmid for the expression of core-streptavidin-FP-3 protein in *E. coli*. It was prepared by insertion of the following 232 bp long NheI/CelII-F3 gene segment (encoding the F3 polypeptide SEQ ID NO: 86)

```
  1 gctagcggca aatctggtac tgaagccgcg ggtgctatgt 41 tcctggaggc gatcccgatg tccggaggtg gcggttctgg 81 cggtggtggc tccggtggtg gtggcaccac gtgggaagca 121 tgggaccgtg ctatcgcaga atacgcggct cgcatcgaag 161 ctttgatccg tgcagctcag gagcagcagg aacgtaacga 201 agcagcgctg cgtgaactgt aatgagctga gc
``` into the 3547 bp long NheI/CelII-4980 plasmid fragment.

Example 2

Expression of the Core-streptavidin Fusion Proteins in *E. Coli*

For the expression of the core-streptavidin fusion proteins 4981, 4982, and 4983 an *E. coli* host/vector system was employed which enables an antibiotic-free plasmid selection by complementation of an *E. coli* auxotrophy (PyrF) (see e.g. EP-B 0 972 838 and U.S. Pat. No. 6,291,245).

The fusion proteins were expressed in the *E. coli* strain CSPZ-2 (leuB, proC, trpE, thi-1, ΔpyrF).

Transformation and Cell Culturing by Complementation of a pyrF Auxotrophy in Selective Medium The *E. coli* K12 strain CSPZ-2 (leuB, proC, trpE, thi-1, ΔpyrF) was transformed with the expression plasmids (4981, 4982, and 4983, respectively) obtained in previous step. The transformed CSPZ-2 cells were first grown at 37° C. on agar plates and subsequently in a shaking culture in M9 minimal medium containing 0.5% casamino acids (Difco) up to an optical density at 550 nm (OD550) of 0.6-0.9 and subsequently induced with IPTG (1-5 mmol/l final concentration).

After an induction phase of 4 to 16 hours at 37° C. the cells were harvested by centrifugation, washed with 50 mmol/l potassium phosphate buffer, pH 6.5, and stored at −20° C. until further processing.

Expression Analysis

For expression analysis cell pellets from 3 OD550 nm units (1 OD550 nm=1 ml cell suspension with an OD at 550 nm of 1) of centrifuged culture medium were re-suspended in 0.25 ml 10 mmol/l potassium phosphate buffer, pH 6.5, and the cells were lysed by ultrasonic treatment (two pulses of 30 sec. at 50% intensity). The insoluble cell components were sedimented (centrifugation 14,000 rpm, 5 min.) and the supernatant was admixed with 1/5 of its volume 5×SDS sample buffer (1×SDS sample buffer: 50 mmol/l Tris-HCl, pH 6.8, 1% SDS, 50 mmol/l DTT, 10% glycerol, 0.001% bromophenol blue). The insoluble cell debris fraction (pellet) was re-suspended in 0.3 ml 1×SDS sample buffer, the samples were incubated for 5 min. at 95° C. and centrifuged again. Subsequently, the proteins were separated by SDS polyacrylamide gel electrophoresis (PAGE) (Laemmli, U. K., Nature 227 (1970) 680-685) and stained with Coomassie Brilliant Blue R dye.

The synthesized core-streptavidin fusion protein was homogeneous and was found exclusively in the insoluble cell debris fraction in the form of insoluble protein aggregates, the so-called inclusion bodies (IBs). The expression yield was comparable within the scope of the measurement accuracy in all clones and was between 30%-60% relative to the total *E. coli* protein.

Example 3

10 Liter High Cell Density Fermentations of *E. coli* for the Recombinant Production of the Core-streptavidin Fusion Proteins Pre-culture:

In order to prepare the pre-culture, 300 ml M9-plus medium (M9 medium supplemented with 0.5% casamino acids and 0.9 g/l Trp, Pro and Leu each) was inoculated with 1 ml of a glycerol stock of *E. coli* CSPZ-2 transformed with plasmid 4981, 4982, and 4983, respectively, in a 1000 ml Erlenmeyer flask. The culture was incubated for about 6 hours at 37° C. on an excenter shaker with 150 rpm until an OD578 nm of 3.0 was reached.

101 Fed-batch Main Fermentation:

At the beginning of fermentation, the pre-culture was transferred into the 10 liter fermenter. The main culture was grown in defined M9 salt medium containing 1.4% glycerol instead of glucose, 2% casamino acids and 0.1% of the amino acids Trp, Leu and Pro each, up to an OD578 nm of 20. Subsequently, feeding of the culture with a glycerol yeast dosage (stock solution: 30% yeast extract and 33% glycerol) was started, the flow rate of which was varied between 0.8 and 3.5 ml/min depending on the development of the pH value of the culture, thereby avoiding any further addition of correction fluids ($H_3PO_4$, KOH). The pH was maintained at pH 7.0, the $pO_2$ value was held at 50% by controlling the stirrer speed. At an OD578 nm of 70 1.5 mmol/l IPTG was added. The fermentation was terminated at an OD578 nm of 160-180.

Harvesting the Biomass:

The content of the fermenter was centrifuged with a flow-through centrifuge (13,000 rpm, 13 l/h) and the harvested biomass was stored at −20° C. until further processing.

Example 4

Cell Lysis and Preparation of Inclusion Bodies (IBs)

200 g E. coli cells (wet weight) were suspended in one liter 0.1 mol/l Tris-HCl, pH 7.0, at 0° C., 300 mg lysozyme were added and incubated for 20 minutes at 0° C. Subsequently, the cells were completely lysed mechanically by means of high pressure dispersion and the DNA was digested for 30 minutes at 25° C. by adding 2 ml 1 mol/1MgCl$_2$ and 10 mg DNAse. Thereafter, 500 ml 60 mmol/l EDTA, 6% Triton X-100 and 1.5 mol/l NaCl, pH 7.0 were admixed with the lysis solution and incubated for another 30 minutes at 0° C. Subsequently, the insoluble components (cell debris and IBs) were sedimented by centrifugation. The pellet was suspended in one liter 0.1 mol/l Tris-HCl, 20 mmol/l EDTA, pH 6.5, incubated for 30 minutes at 25° C. and the IB preparation was isolated by centrifugation.

Example 5

Solubilization of the F1, F2, and F3 Containing Core-streptavidin Fusion Proteins, Enzymatic Release and Purification of the F1, F2 and F3 Polypeptide The inclusion bodies obtained in the previous example were washed two times each with 100 mM potassium phosphate buffer pH 6.5, 500 mM sodium chloride with 20 mM EDTA, and double distilled water. One gram (wet weight) of pelleted inclusion bodies was dissolved by the addition of 10 ml 30 mM potassium hydroxide solution. After 30 min. of stirring the pH value was changed to pH 8.9 by the addition of 1 M boric acid. After solubilization and pH adjustment the F1 and F2 containing core-streptavidin fusion proteins were enzymatically digested with trypsin (1:25000 w/w) while the F3 containing core-streptavidin fusion protein was enzymatically digested with LysC (1:20000 w/w; 10 μl of a 10 μM LysC solution). The solution was incubated at 15° C. over night. The trypsin digestion was stopped by the addition of a 10-fold molar excess of aprotinin. Residual protease was purified away by rec SerETI affinity chromatography. The LysC digestion of F3 was stopped by rec SerETI affinity chromatography only.

The released F1, F2 and F3 fusion polypeptide was purified by reversed phase chromatography using a Eurospher C8 chromatography column.

Example 6

Formation of the Protein Complex of Fusion Polypeptide and Alpha1-antitrypsin

25 μM alpha1-antitrypsin in PBS (phosphate buffered saline, 1 mM $KH_2PO_4$, 10 mM $Na_2HPO_4$, 105 mM NaCl, 2.7 mM KCl) were incubated at 37° C. with four to five times excess of the fusion polypeptide (e.g. 125 μM) for 24 hours. Using a longer incubation time did not result in the further formation of the protein complex. After the incubation the protein complex was separated from non-complexed serpin-finger polypeptide by size exclusion filtration. Fractions comprising molecules of approximately the same molecular weight were combined. The combined fractions were concentrated and a sample was applied to an SDS-PAGE gel. The individual bands on the SDS-PAGE gel were analyzed using the 1D-Image-Master (Amersham Bioscience), the fraction of the protein complex was quantified and molecular weight difference were determined. The activity of the combined and concentrated fractions was determined via BIAcore (see FIG. 3). In the reaction mixture dimeric alpha1-antitrypsin (125 kDa, approximately 14%), protein complex (60 kDa, approximately 15%) and monomeric alpha1-antitrypsin (55 kDa) have been detected.

Example 7

BIAcore Analysis

All surface plasmon resonance measurements were performed on a BIAcore 3000 instrument (GE Healthcare Biosciences AB, Sweden) at 25° C. Chemically prepared HIV HR1 peptide (heptad repeat 1; Biotin-QARQLLS-GIVQQQNNLL-RAIEAQQHLLQLTVWGIKQLQARILAVERYLKD Q-NH2 (SEQ ID NO: 87)) was immobilized on a CM5 biosensor chip according to the manufacturer instructions (GE Healthcare Biosciences AB, Sweden). The fusion polypeptide was diluted to a concentration of 25 nM and injected over 5 minutes at a flow rate of 50 μl/min. Thereafter the protein complex obtained from different combined fractions was diluted into the same buffer to concentrations of 250 nM and 80 nM and injected over 5 minutes at a flow rate of 50 μl/min. Afterwards the sensor chip was regenerated for 1 minute with PBS, pH 8.0, 0.005% (v/v) Tween 20. Data analysis was performed with the BIAevaluation software (BIAcore, Sweden) (see FIG. 4).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A fusion polypeptide comprising in an N-terminal to C-terminal direction a serpin-finger polypeptide, wherein the amino acid sequence of the serpin-finger polypeptide is selected from the group consisting of SEQ ID NO:1, 2, 3, 4, 5, 6, 7, 8, 9, 10, 11, 15, 16 ,17, 18, 19, 20, 21, 22, 23, 24, 25, 26, 27, 28, 29, 30, 31, 82, and 83, fused to an HIV fusion inhibitor polypeptide, wherein the amino acid sequence of the HIV fusion inhibitor polypeptide is selected from the group consisting of SEQ ID NO:13, 32, 33, 34, 35, 36, 37, 38, 39, 40, 41, and 42.

2. The fusion polypeptide according to claim 1, wherein the amino acid sequence of the serpin-finger polypeptide is selected from the group consisting of: TEAAGAMFLEA-IVM (SEQ ID NO: 3), TEAAGAMFFEAIPM (SEQ ID NO: 5), SEAAASTAVVIA (SEQ ID NO: 7), TEAAGATAVVIA (SEQ ID NO: 8), and SEAAASMFLEAI (SEQ ID NO: 11).

3. The fusion polypeptide according to claim 2, wherein the amino acid sequence of the serpin-finger polypeptide is selected from the group consisting of: SEAAASTAVVIA (SEQ ID NO: 7) and SEAAASMFLEAI (SEQ ID NO: 11).

4. The fusion polypeptide according to claim 1, wherein the fusion polypeptide further comprises a peptidic linker polypeptide between the serpin-finger polypeptide and the HIV fusion inhibitor polypeptide, wherein the amino acid sequence of the peptidic linker polypeptide is selected from the group consisting of SEQ ID NO:12, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

5. The fusion polypeptide according to claim 1, wherein the fusion polypeptide further comprises a peptidic linker polypeptide between the serpin-finger polypeptide and the HIV fusion inhibitor polypeptide, wherein the amino acid sequence of the peptidic linker polypeptide is GGSGG (SEQ ID NO: 12).

6. The fusion polypeptide according to claim 1, wherein the amino acid sequence of the HIV fusion inhibitor polypeptide is MTWMEWDREINNYTSLIHSLIEESQN-QQEKNEQELLELDKWASLWNWF (SEQ ID NO: 13).

7. The fusion polypeptide of claim 1, wherein the serpin-finger polypeptide comprises the amino acid sequence of SEQ ID NO:83.

8. The fusion polypeptide of claim 1, wherein the HIV fusion inhibitor polypeptide comprises the amino acid sequence of SEQ ID NO:40.

9. The fusion polypeptide of claim 4, wherein the peptidic linker comprises the amino acid sequence of SEQ ID NO:50.

10. A fusion polypeptide comprising in N-terminal to C-terminal direction a serpin-finger polypeptide comprising the amino acid sequence of SEQ ID NO:83, a peptidic linker polypeptide comprising the amino acid sequence of SEQ ID NO:50, and an HIV fusion inhibitor polypeptide comprising the amino acid sequence of SEQ ID NO:40.

11. A fusion polypeptide comprising the amino acid sequence of SEQ ID NO:78.

12. A protein complex comprising the fusion polypeptide according to claim 1 and a serpin.

13. The protein complex of claim 12, wherein the fusion polypeptide is incorporated into the middle of beta-sheet A as strand 4a of the serpin.

14. The protein complex according to claim 12, wherein the serpin is selected from the group consisting of alpha1-antitrypsin and antithrombin.

15. The protein complex according to claim 12, wherein the fusion polypeptide comprises a peptidic linker polypeptide between the serpin-finger polypeptide and the HIV fusion inhibitor polypeptide.

16. The protein complex according to claim 12, wherein the amino acid sequence of the serpin-finger polypeptide is selected from the group consisting of: TEAAGAMFLEA-IVM (SEQ ID NO: 3), TEAAGAMFFEAIPM (SEQ ID NO: 5), SEAAASTAVVIA (SEQ ID NO: 7), TEAAGATAVVIA (SEQ ID NO: 8), and SEAAASMFLEAI (SEQ ID NO: 11).

17. The protein complex according to claim 12, wherein the amino acid sequence of the HIV fusion inhibitor polypeptide is MTWMEWDREINNYTSLIHSLIEESQNQQ EKNEQELLELDKWASLWNWF (SEQ ID NO: 13).

18. The protein complex according to claim 16, wherein:

(a) the amino acid sequence of the serpin-finger polypeptide is: SEAAASTAVVIA (SEQ ID NO: 7) or SEAAASMFLEAI (SEQ ID NO: 11);

(b) the serpin is alpha1-antitrypsin, and;

(c) the amino acid sequence of the peptidic linker is GGSGG (SEQ ID NO: 12).

19. A method of inhibiting the infection of a cell by Human Immunodeficiency Virus (HIV), the method comprising administering an effective amount of the fusion polypeptide according to claim 1.

20. A method of inhibiting the infection of a cell by HIV, the method comprising administering an effective amount of the protein complex according to claim 12.

21. A method of treating an individual having HIV infection, the method comprising administering to the individual an effective amount of the fusion polypeptide according to claim 1.

22. A method of treating an individual having HIV infection, the method comprising administering to the individual an effective amount of the protein complex according to claim 12.

* * * * *

```
SEQUENCE LISTING

<160> NUMBER OF SEQ ID NOS: 94

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      serpin-finger 1

<400> SEQUENCE: 1

Ala Gly Ala Met Phe Leu Glu Ala Ile Val Met
```

```
1               5                    10
```

```
<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      serpin-finger 2

<400> SEQUENCE: 2

Ala Ala Gly Ala Met Phe Leu Glu Ala Ile Val Met
1               5                    10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      serpin-finger 3

<400> SEQUENCE: 3

Thr Glu Ala Ala Gly Ala Met Phe Leu Glu Ala Ile Val Met
1               5                    10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      serpin-finger 4

<400> SEQUENCE: 4

Ala Gly Ala Met Phe Leu Glu Ala Ile Val Met
1               5                    10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      serpin-finger 5

<400> SEQUENCE: 5

Thr Glu Ala Ala Gly Ala Met Phe Phe Glu Ala Ile Pro Met
1               5                    10

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      serpin-finger 6

<400> SEQUENCE: 6

Thr Ala Val Val Ile Ala
1               5

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
```

-continued

```
      serpin-finger 7

<400> SEQUENCE: 7

Ser Glu Ala Ala Ala Ser Thr Ala Val Val Ile Ala
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      serpin-finger 8

<400> SEQUENCE: 8

Thr Glu Ala Ala Gly Ala Thr Ala Val Val Ile Ala
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      serpin-finger 9

<400> SEQUENCE: 9

Thr Asp Ala Ala Gly Ala Thr Ala Val Val Ile Ala
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      serpin-finger 10

<400> SEQUENCE: 10

Ser Asp Ala Ala Gly Ala Met Phe Leu Glu Ala Ile
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      serpin-finger 11

<400> SEQUENCE: 11

Ser Glu Ala Ala Ala Ser Met Phe Leu Glu Ala Ile
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      linker 1

<400> SEQUENCE: 12

Gly Gly Ser Gly Gly
1               5

<210> SEQ ID NO 13
```

```
<211> LENGTH: 48
<212> TYPE: PRT
<213> ORGANISM: Artificial Sequence
<220> FEATURE:
<223> OTHER INFORMATION: Description of Artificial Sequence: Synthetic
      antifusogenic peptide 1

<400> SEQUENCE: 13

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Asp Lys Trp Ala Ser Leu Trp Asn Trp Phe
        35                  40                  45

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 12

<400> SEQUENCE: 14

Thr Ile Asp Glu Lys Gly Thr Glu Ala Ala Gly Ala Met Phe Leu Glu
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 13

<400> SEQUENCE: 15

Asp Val Phe Glu Glu Gly Thr Glu Ala Ser Ala Ala Thr Ala Val Lys
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 14

<400> SEQUENCE: 16

Asp Val Asp Glu Ala Gly Thr Glu Ala Ala Ala Ala Thr Thr Phe Ala
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 15

<400> SEQUENCE: 17

Gln Leu Asn Glu Glu Gly Val Asp Thr Ala Gly Ser Thr Gly Val Thr
1               5                   10                  15

<210> SEQ ID NO 18
<211> LENGTH: 16
<212> TYPE: PRT
<213> ORGANISM: Artificial Sequence
```

-continued

```
<220> FEATURE:
<223> OTHER INFORMATION: Description of Artificial Sequence: Synthetic
      serpin-finger 16

<400> SEQUENCE: 18

His Ile Gly Glu Lys Gly Thr Glu Ala Ala Ala Val Pro Glu Val Glu
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 17

<400> SEQUENCE: 19

Glu Val Asp Glu Arg Gly Thr Glu Ala Val Ala Gly Ile Leu Ser Glu
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 18

<400> SEQUENCE: 20

Glu Val Thr Glu Glu Gly Val Glu Ala Ala Ala Ala Thr Ala Val Val
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 19

<400> SEQUENCE: 21

Glu Val Thr Glu Glu Gly Ala Glu Ala Ala Ala Ala Thr Ala Val Val
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 20

<400> SEQUENCE: 22

Thr Val Asn Glu Glu Gly Thr Gln Ala Thr Thr Val Thr Thr Val Gly
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 21

<400> SEQUENCE: 23

Glu Val Asp Glu Asn Gly Thr Gln Ala Ala Ala Ala Thr Gly Ala Val
1               5                   10                  15
```

```
<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 22

<400> SEQUENCE: 24

Glu Val Asn Glu Glu Gly Thr Glu Ala Ala Ala Ala Thr Ala Val Val
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 23

<400> SEQUENCE: 25

Asp Val Asn Glu Glu Gly Thr Glu Ala Ala Ala Gly Thr Gly Gly Val
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 24

<400> SEQUENCE: 26

Glu Val Asn Glu Ser Gly Thr Val Ala Ser Ser Ser Thr Ala Val Ile
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 25

<400> SEQUENCE: 27

Asp Val Phe Glu Glu Gly Thr Glu Ala Ser Ala Ala Thr Ala Val Lys
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 26

<400> SEQUENCE: 28

Glu Val Thr Glu Glu Gly Thr Glu Ala Thr Ala Ala Thr Gly Ser Asn
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 27
```

```
<400> SEQUENCE: 29

Glu Ile Thr Glu Asp Gly Gly Asp Ser Ile Glu Val Pro Gly Ala Arg
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 28

<400> SEQUENCE: 30

Glu Leu Ser Glu Val Gly Val Glu Ala Ala Ala Thr Ser Ile Ala
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin-finger 29

<400> SEQUENCE: 31

Glu Leu Thr Glu Thr Gly Val Glu Ala Ala Ala Ala Ser Ala Ile Ser
1               5                   10                  15

<210> SEQ ID NO 32
<211> LENGTH: 38
<212> TYPE: PRT
<213> ORGANISM: Artificial Sequence
<220> FEATURE:
<223> OTHER INFORMATION: Description of Artificial Sequence: Synthetic
      antifusogenic peptide 2

<400> SEQUENCE: 32

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys Asp Gln
        35

<210> SEQ ID NO 33
<211> LENGTH: 38
<212> TYPE: PRT
<213> ORGANISM: Artificial Sequence
<220> FEATURE:
<223> OTHER INFORMATION: Description of Artificial Sequence: Synthetic
      antifusogenic peptide 3

<400> SEQUENCE: 33

Gln Gln Glu Lys Asn Glu Gln Asp Leu Leu Ala Leu Asp Lys Trp Ala
1               5                   10                  15

Ser Leu Trp Thr Trp Phe Asp Ile Ser His Trp Leu Trp Tyr Ile Lys
            20                  25                  30

Ile Phe Ile Met Ile Val
        35

<210> SEQ ID NO 34
<211> LENGTH: 34
<212> TYPE: PRT
<213> ORGANISM: Artificial Sequence
<220> FEATURE:
```

```
<223> OTHER INFORMATION: Description of Artificial Sequence: Synthetic
      antifusogenic peptide 4

<400> SEQUENCE: 34

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu

<210> SEQ ID NO 35
<211> LENGTH: 36
<212> TYPE: PRT
<213> ORGANISM: Artificial Sequence
<220> FEATURE:
<223> OTHER INFORMATION: Description of Artificial Sequence: Synthetic
      antifusogenic peptide 5

<400> SEQUENCE: 35

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu
        35

<210> SEQ ID NO 36
<211> LENGTH: 36
<212> TYPE: PRT
<213> ORGANISM: Artificial Sequence
<220> FEATURE:
<223> OTHER INFORMATION: Description of Artificial Sequence: Synthetic
      antifusogenic peptide 6

<400> SEQUENCE: 36

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 37
<211> LENGTH: 39
<212> TYPE: PRT
<213> ORGANISM: Artificial Sequence
<220> FEATURE:
<223> OTHER INFORMATION: Description of Artificial Sequence: Synthetic
      antifusogenic peptide 7

<400> SEQUENCE: 37

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35

<210> SEQ ID NO 38
<211> LENGTH: 39
<212> TYPE: PRT
<213> ORGANISM: Artificial Sequence
<220> FEATURE:
```

```
<223> OTHER INFORMATION: Description of Artificial Sequence: Synthetic
      antifusogenic peptide 8

<400> SEQUENCE: 38

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35

<210> SEQ ID NO 39
<211> LENGTH: 58
<212> TYPE: PRT
<213> ORGANISM: Artificial Sequence
<220> FEATURE:
<223> OTHER INFORMATION: Description of Artificial Sequence: Synthetic
      antifusogenic peptide 9

<400> SEQUENCE: 39

Met Arg Gly Ser His His His His His His Ala Ile Asp Val Ile Glu
1               5                   10                  15

Gly Arg Trp Gln Glu Trp Glu Gln Lys Ile Thr Ala Leu Leu Glu Gln
            20                  25                  30

Ala Gln Ile Gln Gln Glu Lys Asn Glu Tyr Glu Leu Gln Lys Leu Asp
        35                  40                  45

Lys Trp Ala Ser Leu Trp Glu Trp Phe Gly
    50                  55

<210> SEQ ID NO 40
<211> LENGTH: 38
<212> TYPE: PRT
<213> ORGANISM: Artificial Sequence
<220> FEATURE:
<223> OTHER INFORMATION: Description of Artificial Sequence: Synthetic
      antifusogenic peptide 10

<400> SEQUENCE: 40

Thr Thr Trp Glu Ala Trp Asp Arg Ala Ile Ala Glu Tyr Ala Ala Arg
1               5                   10                  15

Ile Glu Ala Leu Ile Arg Ala Ala Gln Glu Gln Gln Glu Lys Asn Glu
            20                  25                  30

Ala Ala Leu Arg Glu Leu
        35

<210> SEQ ID NO 41
<211> LENGTH: 123
<212> TYPE: PRT
<213> ORGANISM: Artificial Sequence
<220> FEATURE:
<223> OTHER INFORMATION: Description of Artificial Sequence: Synthetic
      antifusogenic peptide 11

<400> SEQUENCE: 41

Val Gln Ala Arg Gln Leu Leu Ser Gly Ile Val Gln Gln Gln Asn Asn
1               5                   10                  15

Leu Leu Arg Ala Ile Glu Gly Gln Gln His Leu Leu Gln Leu Thr Val
            20                  25                  30

Trp Gly Pro Lys Gln Leu Gln Ala Arg Ile Leu Ala Val Glu Arg Tyr
        35                  40                  45

Leu Lys Asp Gln Gln Leu Leu Gly Ile Trp Gly Cys Ser Gly Lys Leu
    50                  55                  60
```

Ile Cys Thr Thr Ala Val Pro Trp Asn Ala Ser Trp Ser Asn Lys Ser
 65                  70                  75                  80

Leu Glu Gln Ile Trp Asn Asn Met Thr Trp Met Glu Trp Asp Arg Glu
                 85                  90                  95

Ile Asn Asn Tyr Thr Ser Leu Ile His Ser Leu Ile Glu Glu Ser Gln
            100                 105                 110

Asn Gln Gln Glu Lys Asn Glu Gln Glu Leu Leu
        115                 120

<210> SEQ ID NO 42
<211> LENGTH: 132
<212> TYPE: PRT
<213> ORGANISM: Artificial Sequence
<220> FEATURE:
<223> OTHER INFORMATION: Description of Artificial Sequence: Synthetic
      antifusogenic peptide 12

<400> SEQUENCE: 42

Met Gly Ala Ala Ser Met Thr Leu Thr Val Gln Ala Arg Gln Leu Leu
1               5                   10                  15

Ser Gly Ile Val Gln Gln Gln Asn Asn Glu Leu Arg Ala Ile Glu Gly
            20                  25                  30

Gln Gln His Leu Glu Gln Leu Thr Val Trp Gly Pro Lys Gln Leu Gln
        35                  40                  45

Ala Arg Glu Leu Ala Val Glu Arg Tyr Leu Lys Asp Gln Gln Leu Leu
    50                  55                  60

Gly Ile Trp Gly Cys Ser Gly Lys Leu Ile Cys Thr Thr Ala Val Pro
65                  70                  75                  80

Trp Asn Ala Ser Trp Ser Asn Lys Ser Leu Glu Gln Ile Trp Asn Asn
                85                  90                  95

Met Thr Trp Met Glu Trp Asp Arg Glu Ile Asn Asn Tyr Thr Ser Leu
            100                 105                 110

Ile His Ser Leu Ile Glu Glu Ser Gln Asn Gln Gln Glu Lys Asn Glu
        115                 120                 125

Gln Glu Leu Leu
    130

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      linker 2

<400> SEQUENCE: 43

Leu Ser Leu Ser Pro Gly Lys
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      linker 3

<400> SEQUENCE: 44

Leu Ser Pro Asn Arg Gly Glu Cys
1               5

```
<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      linker 4

<400> SEQUENCE: 45

Gly Gln Gln Gln Gln Gly Gln Gln Gln Gly Gln Gln Gln Gln
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      linker 5

<400> SEQUENCE: 46

Gly Gln Gln Gln Gln Gly Gln Gln Gln Gln Gly Gln Gln Gln Gln Gly
1               5                   10                  15

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      linker 6

<400> SEQUENCE: 47

Gly Gln Gln Gln Gln Gly Gln Gln Gln Gln Gly Gln Gln Gln Gln Gly
1               5                   10                  15

Asn Asn

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      linker 7

<400> SEQUENCE: 48

Gly Gly Gly Ser Gly Gly Gly Ser Gly Gly Gly Gly Ser Gly Gly
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      linker 8

<400> SEQUENCE: 49

Gly Gly Gly Ser Gly Gly Gly Ser Gly Gly Gly Gly Ser Gly Asn
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
                         linker 9

<400> SEQUENCE: 50

Ser Gly Gly Gly Gly Ser Gly Gly Gly Gly Ser Gly Gly Gly
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      linker 10

<400> SEQUENCE: 51

Ser Gly Gly Gly Gly Ser Gly Gly Gly Gly Ser Gly Gly Gly Gly
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      linker 11

<400> SEQUENCE: 52

Ser Gly Gly Gly Gly Ser Gly Gly Gly Gly Ser Gly Gly Gly Thr
1               5                   10                  15

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      linker 12

<400> SEQUENCE: 53

Ser Gly Gly Gly Gly Ser Gly Gly Gly Gly Ser Gly Gly Gly Gly
1               5                   10                  15

Gly

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      linker 13

<400> SEQUENCE: 54

Ser Gly Gly Gly Gly Ser Gly Gly Gly Gly Ser Gly Gly Gly Gly
1               5                   10                  15

Gly Thr

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      linker 14

<400> SEQUENCE: 55

Ser Gly Gly Gly Gly Ser Gly Gly Gly Gly Ser Gly Gly Gly Gly Gly
```

```
1               5                   10                  15
Gly Asn

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      linker 15

<400> SEQUENCE: 56

Ser Gly Gly Gly Gly Ser Gly Gly Gly Gly Ser Gly Gly Gly Gly
1               5                   10                  15

Ala Ser

<210> SEQ ID NO 57
<211> LENGTH: 25
<212> TYPE: PRT
<213> ORGANISM: Artificial Sequence
<220> FEATURE:
<223> OTHER INFORMATION: Description of Artificial Sequence: Synthetic
      linker 16

<400> SEQUENCE: 57

Ser Gly Gly Gly Gly Ser Gly Gly Gly Gly Ser Gly Gly Gly Ser
1               5                   10                  15

Gly Gly Gly Gly Ser Gly Gly Gly Gly
            20                  25

<210> SEQ ID NO 58
<211> LENGTH: 26
<212> TYPE: PRT
<213> ORGANISM: Artificial Sequence
<220> FEATURE:
<223> OTHER INFORMATION: Description of Artificial Sequence: Synthetic
      linker 17

<400> SEQUENCE: 58

Ser Gly Gly Gly Gly Ser Gly Gly Gly Gly Ser Gly Gly Gly Ser
1               5                   10                  15

Gly Gly Gly Gly Ser Gly Gly Gly Gly Gly
            20                  25

<210> SEQ ID NO 59
<211> LENGTH: 27
<212> TYPE: PRT
<213> ORGANISM: Artificial Sequence
<220> FEATURE:
<223> OTHER INFORMATION: Description of Artificial Sequence: Synthetic
      linker 18

<400> SEQUENCE: 59

Ser Gly Gly Gly Gly Ser Gly Gly Gly Gly Ser Gly Gly Gly Ser
1               5                   10                  15

Gly Gly Gly Gly Ser Gly Gly Gly Gly Gly Gly
            20                  25

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Synthetic
      linker 19
```

<400> SEQUENCE: 60

Ser Gly Gly Gly Ser Gly Gly Gly Ser Gly Gly Gly Ser
1               5                   10                  15

Gly Gly Gly Gly Ser Gly Gly Gly Gly Gly Ala Ser
            20                  25

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      linker 20

<400> SEQUENCE: 61

Gly Ser Ser Ser Ser Ser Ser Ser Ser Ser Ser Ser Ser Ser Ser Ser
1               5                   10                  15

Gly

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic
      linker 21

<400> SEQUENCE: 62

Gly Ser Ser Ser Ser Ser Ser Ser Ser Ser Ser Ser Ser Ser Ser Ser
1               5                   10                  15

Gly Ala Ser

<210> SEQ ID NO 63
<211> LENGTH: 3
<212> TYPE: PRT
<213> ORGANISM: Artificial Sequence
<220> FEATURE:
<223> OTHER INFORMATION: Description of Artificial Sequence: Synthetic
      linker 24

<400> SEQUENCE: 63

Gly Ser Thr
1

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: Synthetic
      linker 25

<400> SEQUENCE: 64

Gly Gly Gly Gly Ser Gly Gly Gly Gly Ser Gly Gly Gly Gly Ser Gly
1               5                   10                  15

Ala Ser

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      linker 26

```
<400> SEQUENCE: 65

Gly Gly Gly Gly Ser Gly Gly Gly Gly Ser Gly Gly Gly Gly Ser Gly
1               5                   10                  15

<210> SEQ ID NO 66
<211> LENGTH: 26
<212> TYPE: PRT
<213> ORGANISM: Artificial Sequence
<220> FEATURE:
<223> OTHER INFORMATION: Description of Artificial Sequence: Synthetic
      linker 27

<400> SEQUENCE: 66

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly
            20                  25

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      linker 28

<400> SEQUENCE: 67

Gly Gly Gly Gly Ser Gly Gly Gly Gly Ser Gly Gly Gly Gly Ser Gly
1               5                   10                  15

Gly

<210> SEQ ID NO 68
<211> LENGTH: 27
<212> TYPE: PRT
<213> ORGANISM: Artificial Sequence
<220> FEATURE:
<223> OTHER INFORMATION: Description of Artificial Sequence: Synthetic
      linker 29

<400> SEQUENCE: 68

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly
            20                  25

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      linker 30

<400> SEQUENCE: 69

Leu Ser Leu Ser Gly Gly
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      linker 31
```

```
<400> SEQUENCE: 70

Leu Ser Leu Ser Pro Gly Gly
1               5

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic
      linker 32

<400> SEQUENCE: 71

Gly Gly Gly Ser Gly Gly Gly Ser Gly Gly Gly Ser Gly Gly Gly Ser
1               5                   10                  15

Gly Gly Gly Ser
            20

<210> SEQ ID NO 72
<211> LENGTH: 23
<212> TYPE: PRT
<213> ORGANISM: Artificial Sequence
<220> FEATURE:
<223> OTHER INFORMATION: Description of Artificial Sequence: Synthetic
      linker 33

<400> SEQUENCE: 72

Gly Gly Gly Ser Gly Gly Gly Ser Gly Gly Gly Ser Gly Gly Gly Ser
1               5                   10                  15

Gly Gly Gly Ser Gly Gly Gly
            20

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      linker 34

<400> SEQUENCE: 73

Gly Gly Gly Ser Gly Gly Gly Gly Ser Gly Gly Gly Ser Gly
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic
      linker 35

<400> SEQUENCE: 74

Gly Gly Gly Ser Gly Gly Gly Gly Ser Gly Gly Gly Ser Gly Gly
1               5                   10                  15

<210> SEQ ID NO 75
<211> LENGTH: 3
<212> TYPE: PRT
<213> ORGANISM: Artificial Sequence
<220> FEATURE:
<223> OTHER INFORMATION: Description of Artificial Sequence: Synthetic
      linker 36

<400> SEQUENCE: 75

Ser Thr Thr
```

-continued

1

<210> SEQ ID NO 76
<211> LENGTH: 71
<212> TYPE: PRT
<213> ORGANISM: Artificial Sequence
<220> FEATURE:
<223> OTHER INFORMATION: Description of Artificial Sequence: Synthetic alpha1-antitrypsin binder construct 1

<400> SEQUENCE: 76

```
Gly Arg Thr Glu Ala Ala Gly Ala Met Phe Leu Glu Ala Ile Pro Met
1               5                   10                  15

Ser Gly Gly Gly Gly Ser Gly Gly Gly Gly Ser Gly Gly Gly Gly Thr
            20                  25                  30

Trp Gln Glu Trp Glu Gln Lys Ile Thr Ala Leu Leu Glu Gln Ala Gln
        35                  40                  45

Ile Gln Gln Glu Lys Asn Glu Tyr Glu Leu Gln Lys Leu Asp Lys Trp
    50                  55                  60

Ala Ser Leu Trp Glu Trp Phe
65                  70
```

<210> SEQ ID NO 77
<211> LENGTH: 54
<212> TYPE: PRT
<213> ORGANISM: Artificial Sequence
<220> FEATURE:
<223> OTHER INFORMATION: Description of Artificial Sequence: Synthetic alpha1-antitrypsin binder construct 2

<400> SEQUENCE: 77

```
Gly Arg Gly Thr Glu Ala Ala Gly Ala Met Phe Leu Glu Ala Ile Pro
1               5                   10                  15

Met Ser Thr Thr Trp Met Glu Trp Asp Lys Glu Ile Asn Asn Tyr Thr
            20                  25                  30

Ser Leu Ile His Ser Leu Ile Glu Glu Ser Gln Asn Gln Gln Glu Lys
        35                  40                  45

Asn Glu Gln Glu Leu Leu
    50
```

<210> SEQ ID NO 78
<211> LENGTH: 71
<212> TYPE: PRT
<213> ORGANISM: Artificial Sequence
<220> FEATURE:
<223> OTHER INFORMATION: Description of Artificial Sequence: Synthetic alpha1-antitrypsin binder construct 3

<400> SEQUENCE: 78

```
Gly Lys Ser Gly Thr Glu Ala Ala Gly Ala Met Phe Leu Glu Ala Ile
1               5                   10                  15

Pro Met Ser Gly Gly Gly Gly Ser Gly Gly Gly Gly Ser Gly Gly Gly
            20                  25                  30

Gly Thr Thr Trp Glu Ala Trp Asp Arg Ala Ile Ala Glu Tyr Ala Ala
        35                  40                  45

Arg Ile Glu Ala Leu Ile Arg Ala Ala Gln Glu Gln Gln Glu Arg Asn
    50                  55                  60

Glu Ala Ala Leu Arg Glu Leu
65                  70
```

<210> SEQ ID NO 79

```
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer N1

<400> SEQUENCE: 79
aaaaaagcgg ccgcgacaat tcgcgcgcga aggcg                                35

<210> SEQ ID NO 80
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer N2

<400> SEQUENCE: 80
aaaaaagcgg ccgctcactg cccgctttcc agtcgg                               36

<210> SEQ ID NO 81
<211> LENGTH: 128
<212> TYPE: PRT
<213> ORGANISM: Homo sapiens

<400> SEQUENCE: 81

Met Ala Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
            20                  25                  30

Glu Ser Ala Val Gly Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Lys Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Lys Ser Thr
            100                 105                 110

Leu Val Gly His Asp Thr Phe Thr Lys Val Lys Pro Ser Ala Ala Ser
        115                 120                 125

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
      serpin Finger

<400> SEQUENCE: 82

Gly Thr Glu Ala Ala Gly Ala Met Phe Leu Glu Ala Ile Pro Met Ser
1               5                   10                  15

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      serpin Finger
```

<400> SEQUENCE: 83

Ser Gly Thr Glu Ala Ala Gly Ala Met Phe Leu Glu Ala Ile Pro Met
1               5                   10                  15

Ser

<210> SEQ ID NO 84
<211> LENGTH: 232
<212> TYPE: DNA
<213> ORGANISM: Artificial Sequence
<220> FEATURE:
<223> OTHER INFORMATION: Description of Artificial Sequence: Synthetic
      FP1 encoding nucleic acid

<400> SEQUENCE: 84
gctagcggtc gtaccgaagc cgcgggcgct atgttcctgg aagcaatccc gatgtccgga      60
ggtggcggtt ctggtggcgg tggttccggc ggtggtggca cgtggcagga atgggaacag     120
aaaatcaccg ctcttctaga acaggcgcag atccagcagg agaaaaacga atacgaactg     180
cagaagcttg acaaatgggc ttctctgtgg aatggttct aatgagctga gc              232

<210> SEQ ID NO 85
<211> LENGTH: 181
<212> TYPE: DNA
<213> ORGANISM: Artificial Sequence
<220> FEATURE:
<223> OTHER INFORMATION: Description of Artificial Sequence: Synthetic
      FP2 encoding nucleic acid

<400> SEQUENCE: 85
gctagcggtc gtggcactga agctgcaggt gcgatgtttc tagaagctat cccgatgtcc      60
accacgtgga tggagtggga caaagaaatc aacaactaca caagcttgat ccactccctg     120
atcgaagaat cccagaacca gcaggagaaa acgaacagg aactgctgta atgagctgag      180
c                                                                     181

<210> SEQ ID NO 86
<211> LENGTH: 232
<212> TYPE: DNA
<213> ORGANISM: Artificial Sequence
<220> FEATURE:
<223> OTHER INFORMATION: Description of Artificial Sequence: Synthetic
      FP3 encoding nucleic acid

<400> SEQUENCE: 86
gctagcggca atctggtac tgaagccgcg ggtgctatgt tcctggaggc gatcccgatg       60
tccggaggtg gcggttctgg cggtggtggc tccggtggtg gtggcaccac gtgggaagca    120
tgggaccgtg ctatcgcaga atacgcggct cgcatcgaag ctttgatccg tgcagctcag    180
gagcagcagg aacgtaacga agcagcgctg cgtgaactgt aatgagctga gc           232

<210> SEQ ID NO 87
<211> LENGTH: 51
<212> TYPE: PRT
<213> ORGANISM: Human immunodeficiency virus

<400> SEQUENCE: 87

Gln Ala Arg Gln Leu Leu Ser Gly Ile Val Gln Gln Asn Asn Leu
1               5                   10                  15

Leu Arg Ala Ile Glu Ala Gln Gln His Leu Leu Gln Leu Thr Val Trp
                20                  25                  30

Gly Ile Lys Gln Leu Gln Ala Arg Ile Leu Ala Val Glu Arg Tyr Leu

```
                35                  40                  45
Lys Asp Gln
    50

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Thr Glu Ala Ala Gly Ala Met Phe Leu Glu Ala Ile Pro
1               5                   10

<210> SEQ ID NO 89
<211> LENGTH: 14
<212> TYPE: PRT
<213> ORGANISM: Homo sapiens

<400> SEQUENCE: 89

Thr Glu Ala Ala Gly Ala Met Phe Leu Glu Ala Ile Val Met
1               5                   10

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Gly Gly Gly Ser
1               5

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Gly Gly Ser Gly
1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Ser Gly Gly Gly
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
        peptide

<400> SEQUENCE: 93

Gln Gln Gln Gln Gly
1               5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 94

Ser Ser Ser Ser Gly
1               5
```